United States Patent
Streit et al.

(10) Patent No.: US 9,962,495 B2
(45) Date of Patent: May 8, 2018

(54) INJECTION DEVICE HAVING A HELICAL OR SPIRAL DOSAGE SCALE

(71) Applicant: TecPharma Licensing AG, Burgdorf (CH)

(72) Inventors: Ursina Streit, Schönbühl (CH); Jürg Hirschel, Bern (CH); Adrian Eich, Wangenried (CH)

(73) Assignee: TecPharma Licensing AG, Burgdorf (CH)

( * ) Notice: Subject to any disclaimer, the term of this patent is extended or adjusted under 35 U.S.C. 154(b) by 582 days.

(21) Appl. No.: 14/599,136

(22) Filed: Jan. 16, 2015

(65) Prior Publication Data

US 2015/0196716 A1    Jul. 16, 2015

Related U.S. Application Data

(63) Continuation of application No. PCT/CH2013/000132, filed on Jul. 17, 2013.

(30) Foreign Application Priority Data

Aug. 1, 2012 (EP) .................................... 12178913

(51) Int. Cl.
*A61M 5/315* (2006.01)
*A61M 5/20* (2006.01)
*A61M 5/31* (2006.01)

(52) U.S. Cl.
CPC .......... *A61M 5/31568* (2013.01); *A61M 5/20* (2013.01); *A61M 5/31553* (2013.01);
(Continued)

(58) Field of Classification Search
CPC ................ A61M 5/20; A61M 5/31568; A61M 5/31541; A61M 5/31553; A61M 5/31585; A61M 5/31593
See application file for complete search history.

(56) References Cited

U.S. PATENT DOCUMENTS

2006/0258988 A1* 11/2006 Keitel ............... A61M 5/31551
                                                           604/181
2006/0270985 A1* 11/2006 Hommann .......... A61M 5/2033
                                                           604/136

FOREIGN PATENT DOCUMENTS

WO   WO 2001/019434   3/2001
WO   WO 2005/018721   3/2005
(Continued)

OTHER PUBLICATIONS

PCT International Search Report dated Oct. 21, 2013 for Application No. PCT/CH2013/000132 (6 pages).

*Primary Examiner* — Rebecca E Eisenberg
(74) *Attorney, Agent, or Firm* — Dorsey & Whitney LLP

(57) ABSTRACT

Driving and dispensing devices for an injection device are used for administering a liquid product and adjusting a product dose and include a dosage display element with a helical dosage scale; an indication device for indicating a dosage value from the dosage scale; and a dosage element, which can be held by a user and screwed relative to the indication device around a rotational axis (L) and relative to the dispensing member along the rotational axis (L) in order to adjust the dosage to be administered. A bearing element having a thread is in a threaded engagement with a thread of the dosage indication element, and the thread pitch of the thread of the dosage indication element is not the same as the pitch (P1) of the helical scale, and may be greater or smaller than the pitch (P1) of the helical scale.

18 Claims, 18 Drawing Sheets

(52) U.S. Cl.
CPC .... *A61M 5/31585* (2013.01); *A61M 5/31593* (2013.01); *A61M 5/31541* (2013.01); *A61M 2005/3126* (2013.01); *A61M 2207/00* (2013.01)

(56) References Cited

FOREIGN PATENT DOCUMENTS

| WO | WO 2005/046770 | 5/2005 |
|----|----------------|--------|
| WO | WO 2009/105909 | 9/2009 |
| WO | WO 2010/049209 | 5/2010 |
| WO | WO 2010/089417 | 8/2010 |
| WO | WO 2010/140974 | 12/2010 |
| WO | WO 2011/060785 | 5/2011 |

* cited by examiner

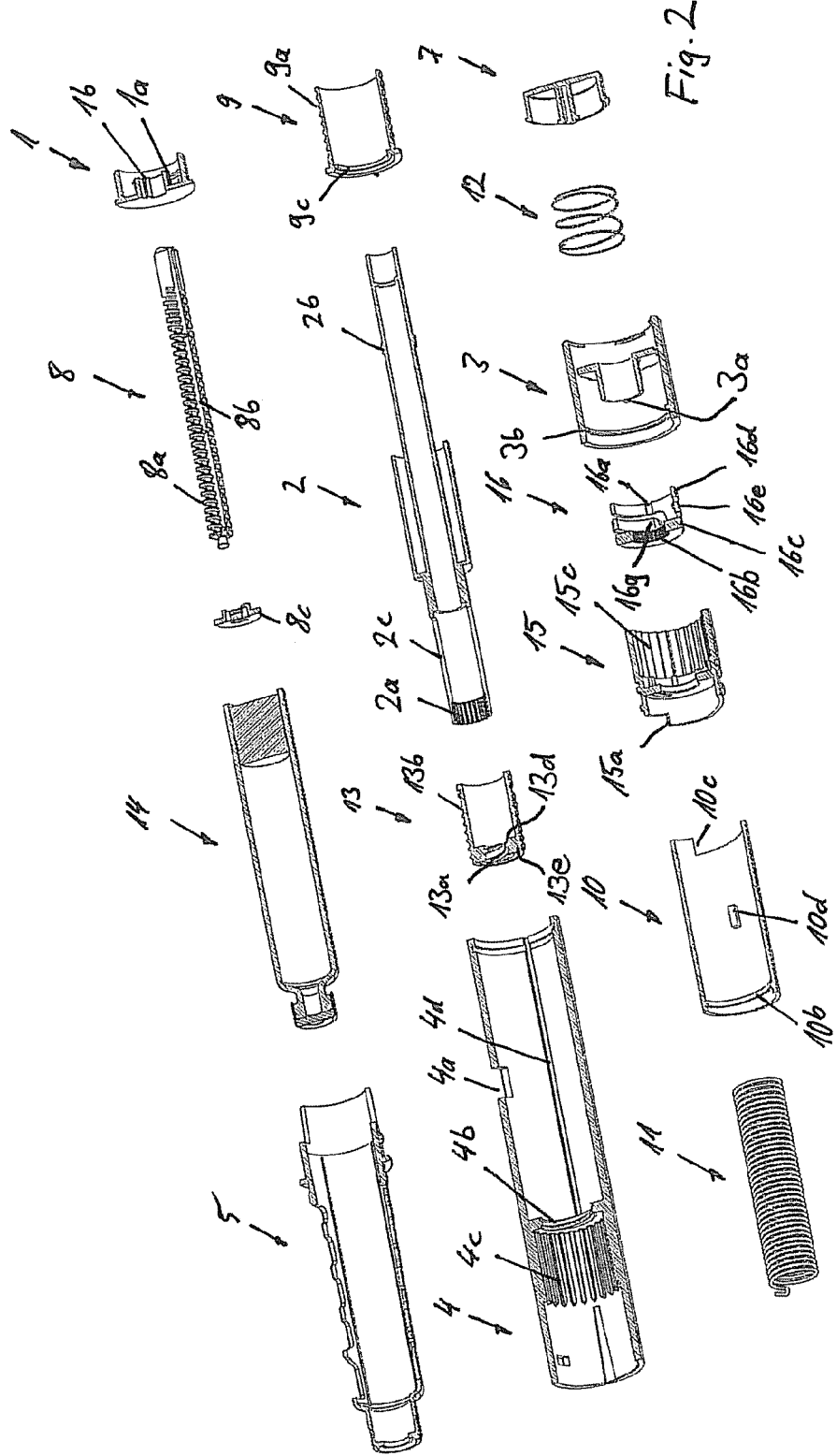

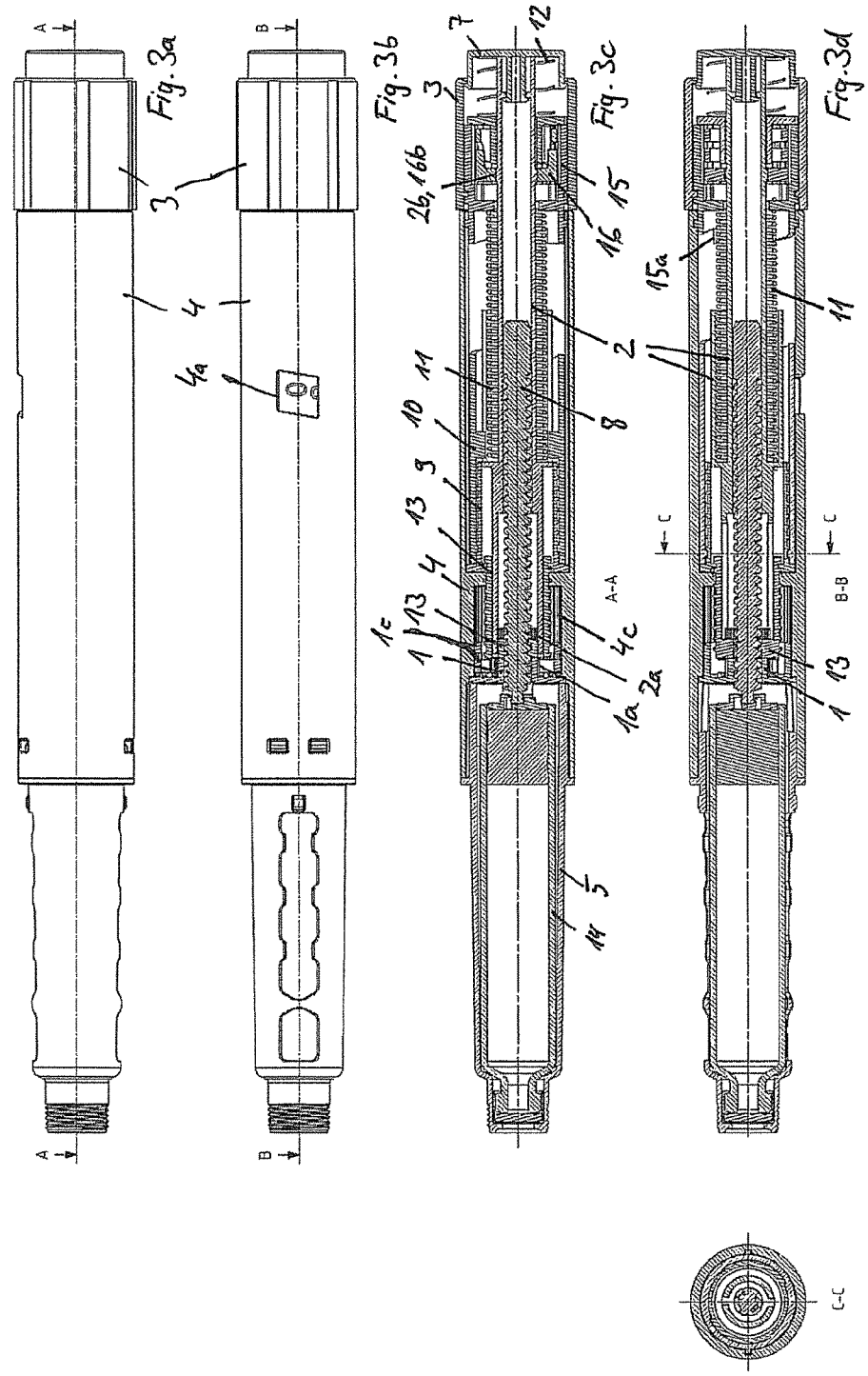

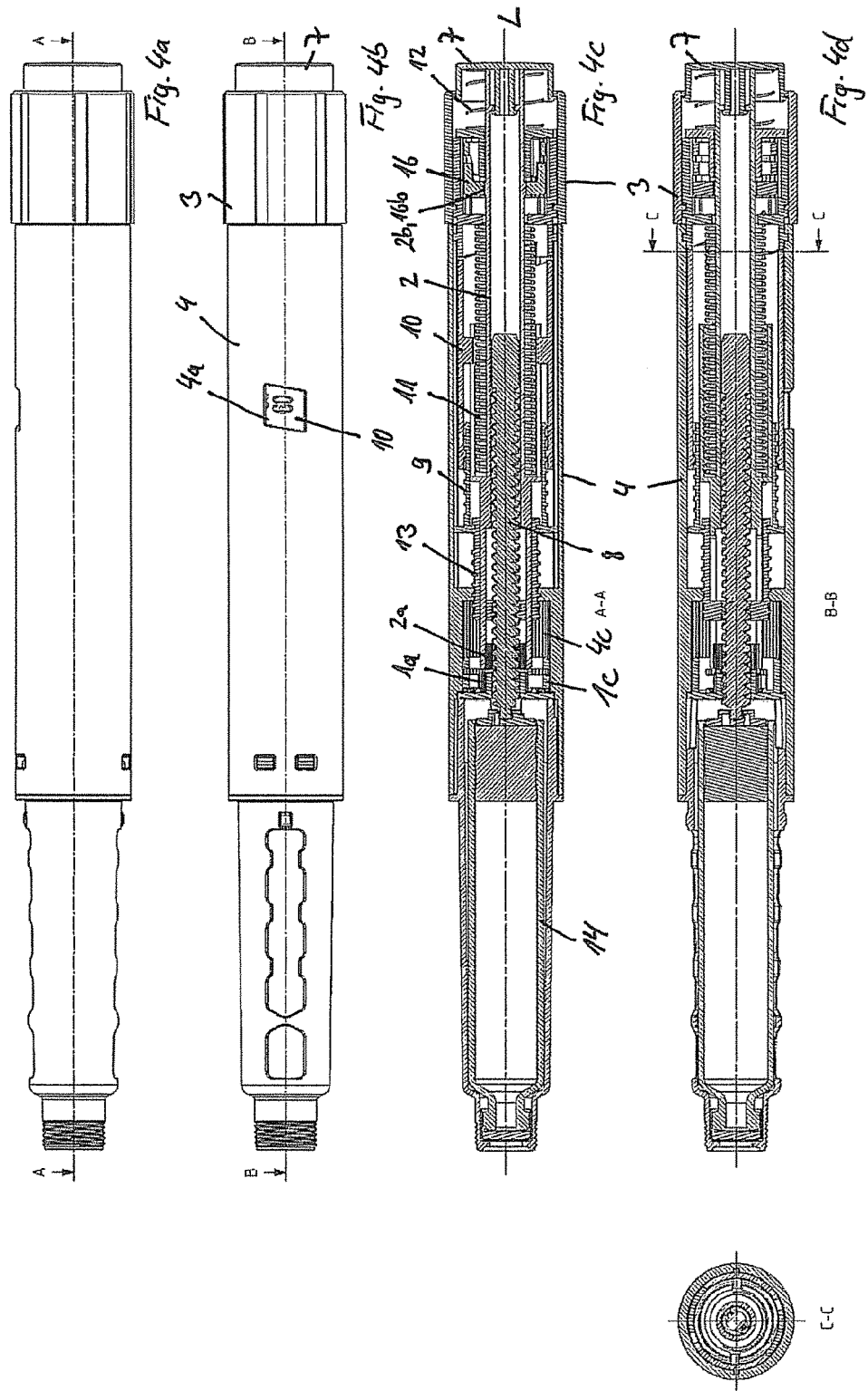

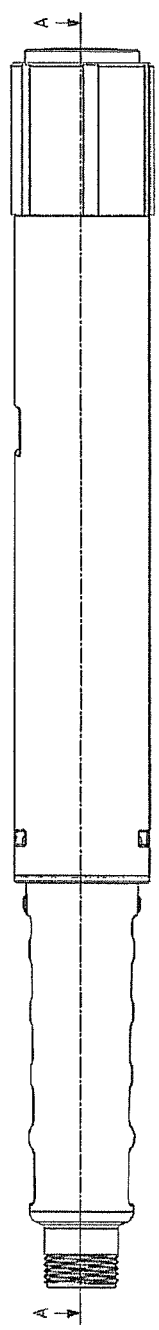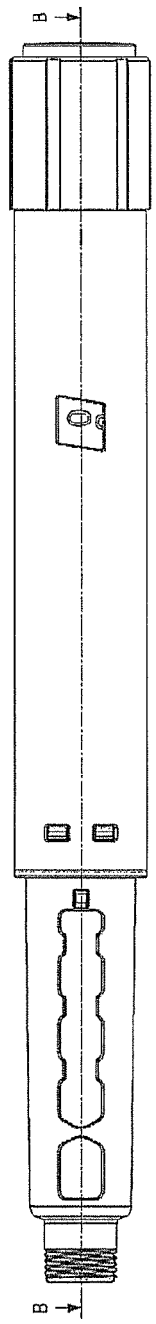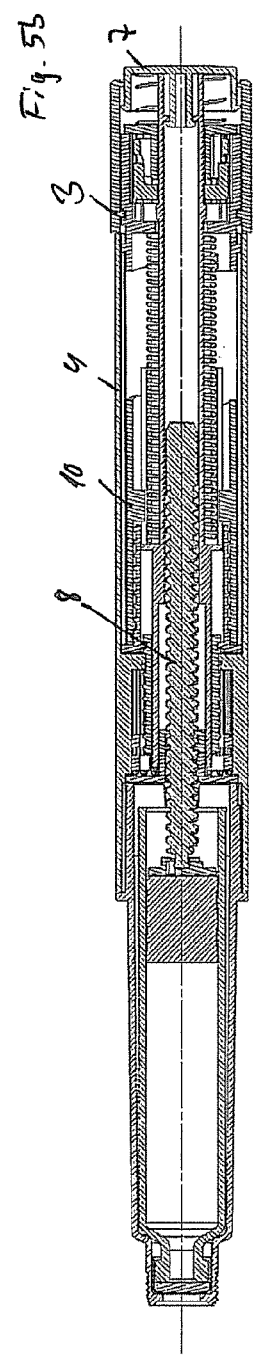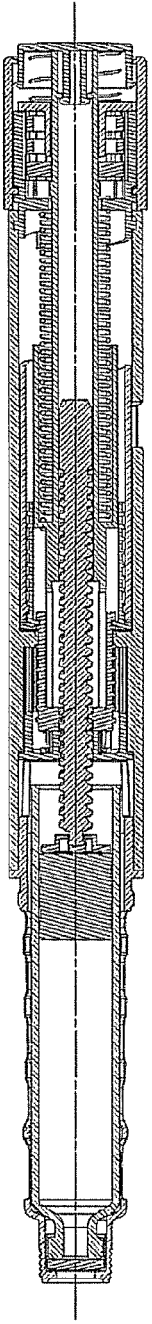

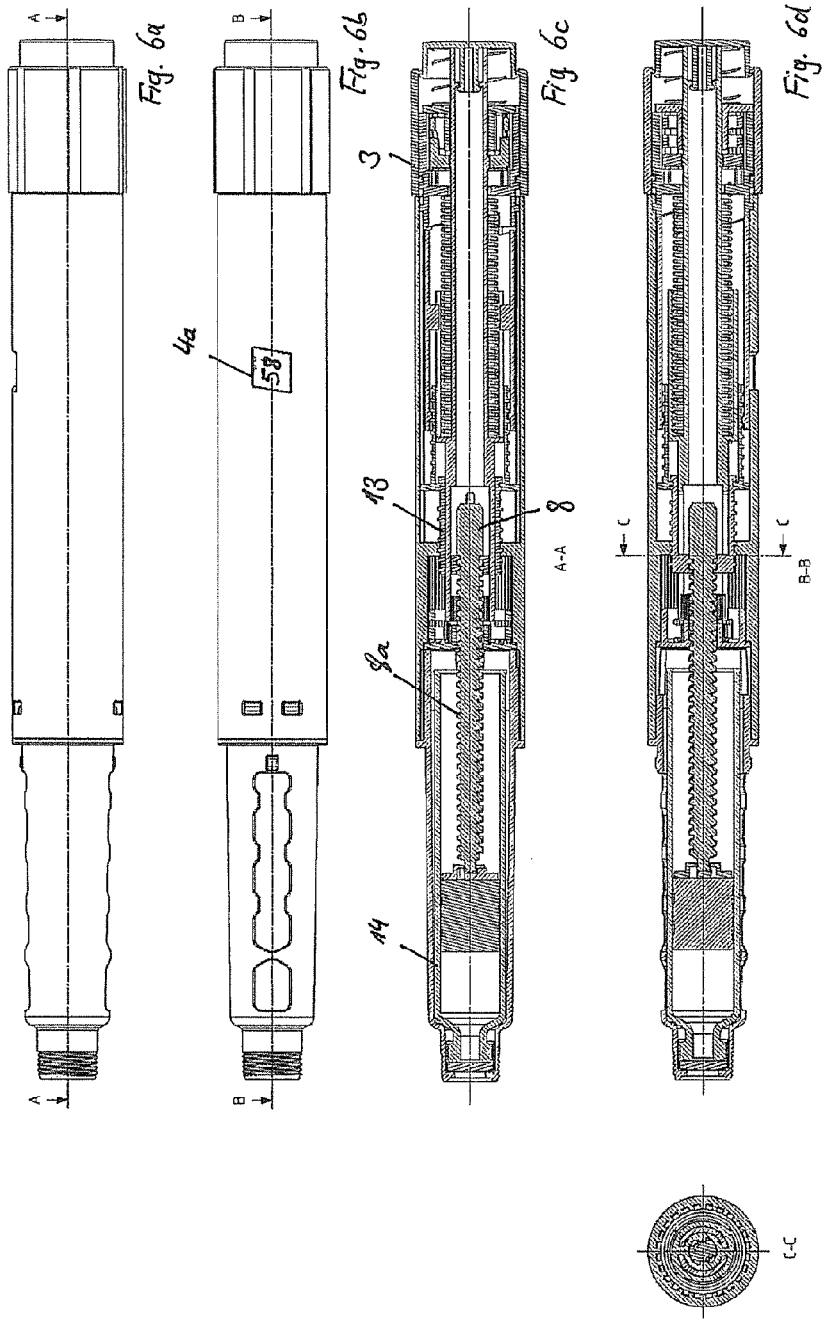

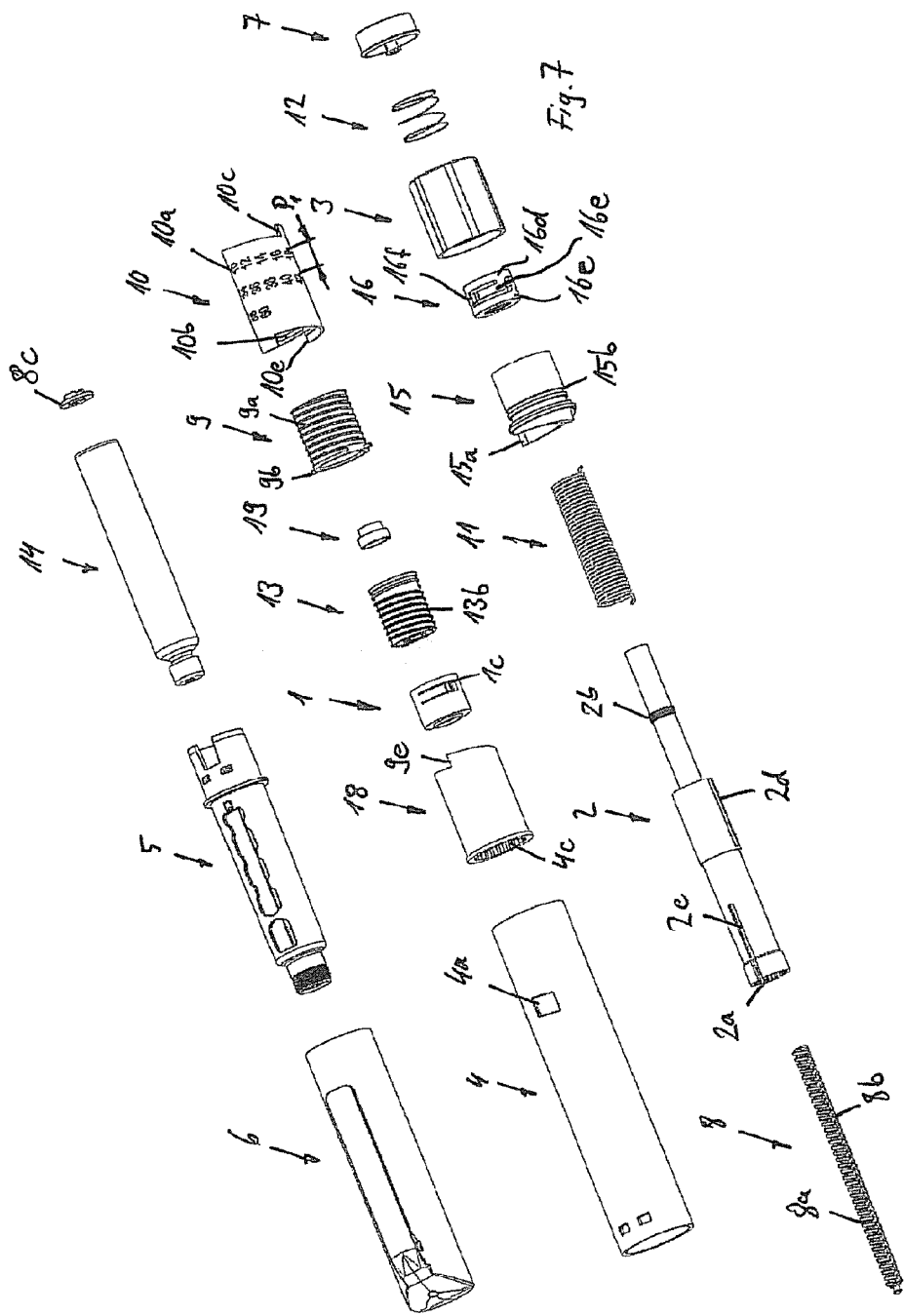

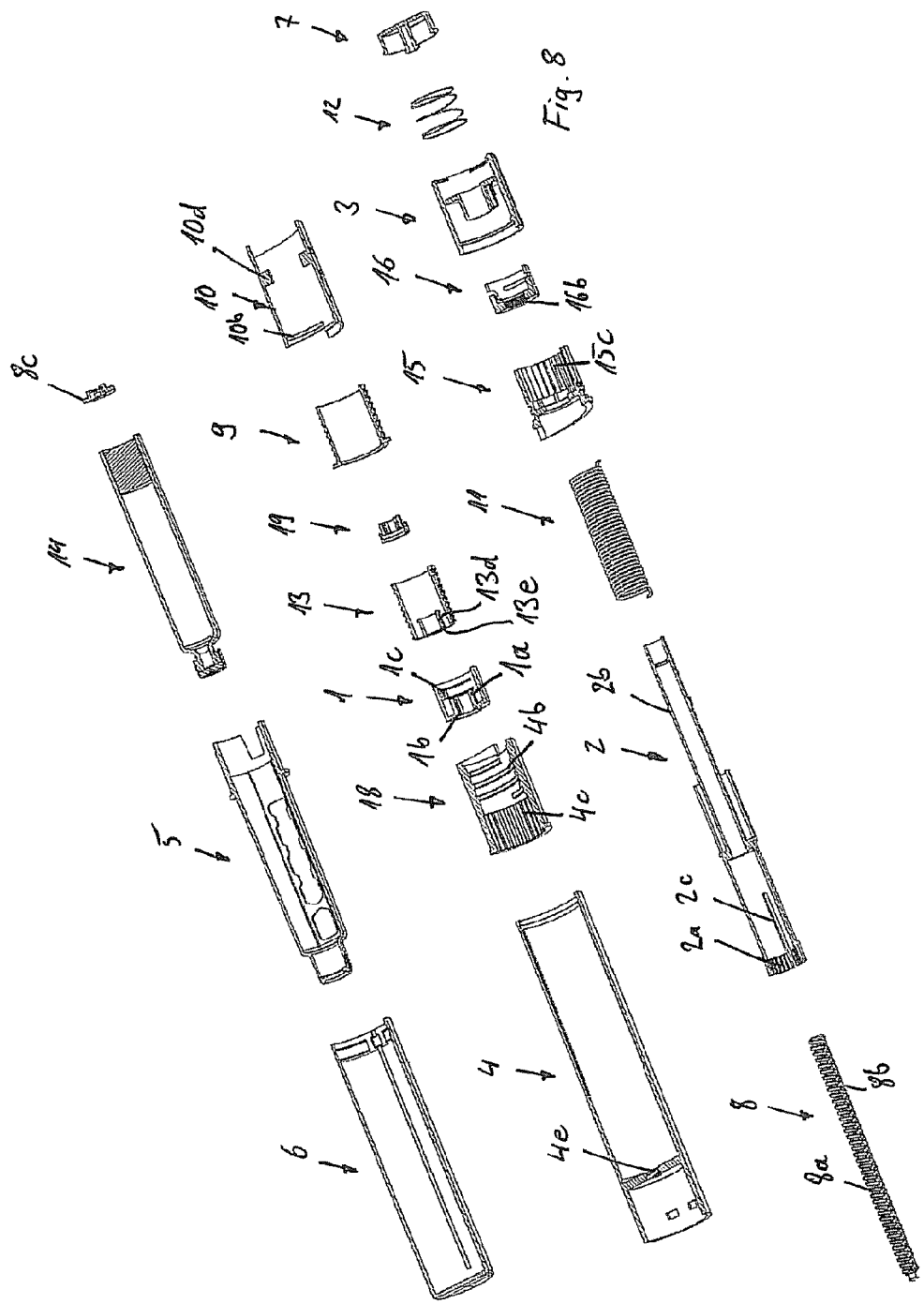

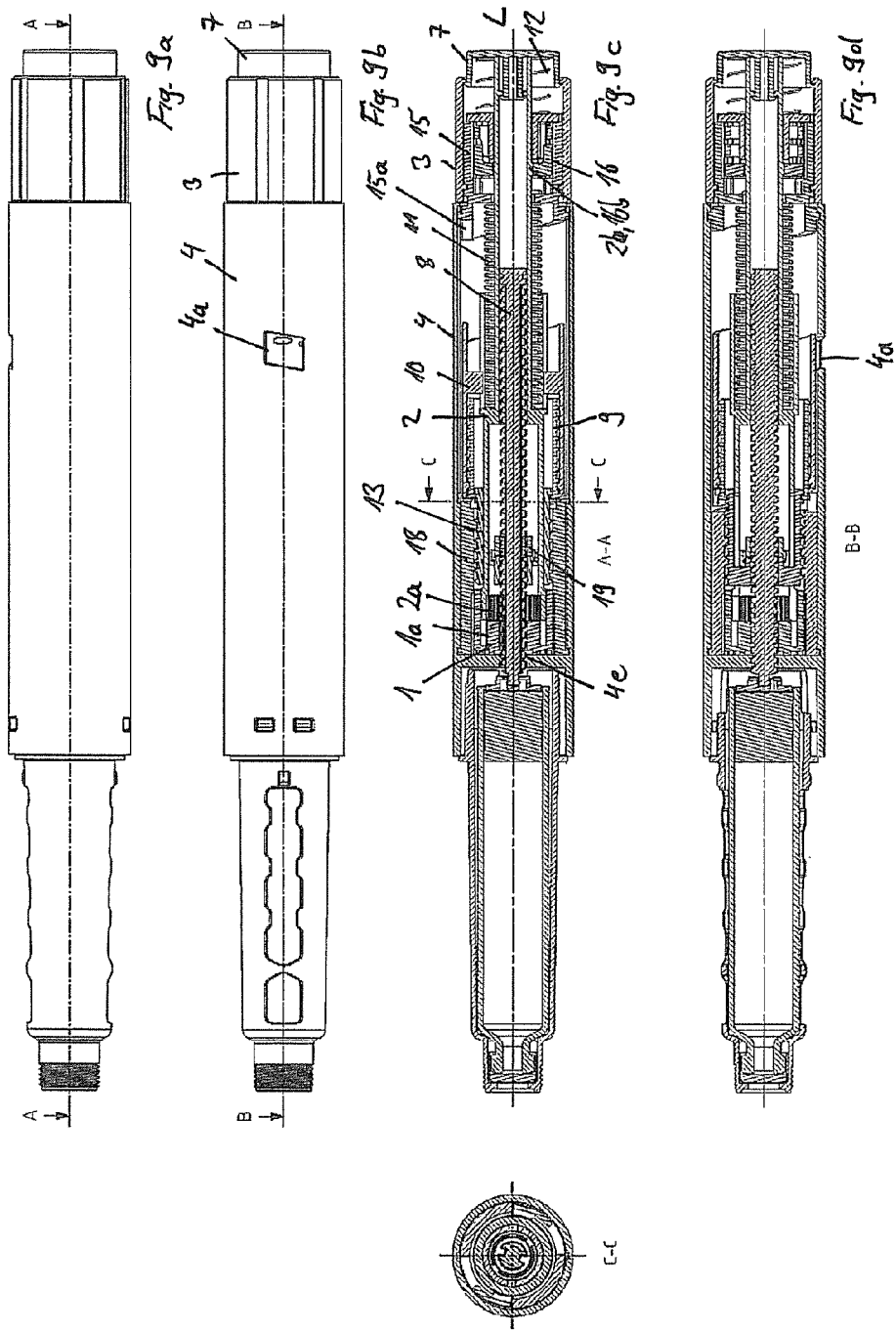

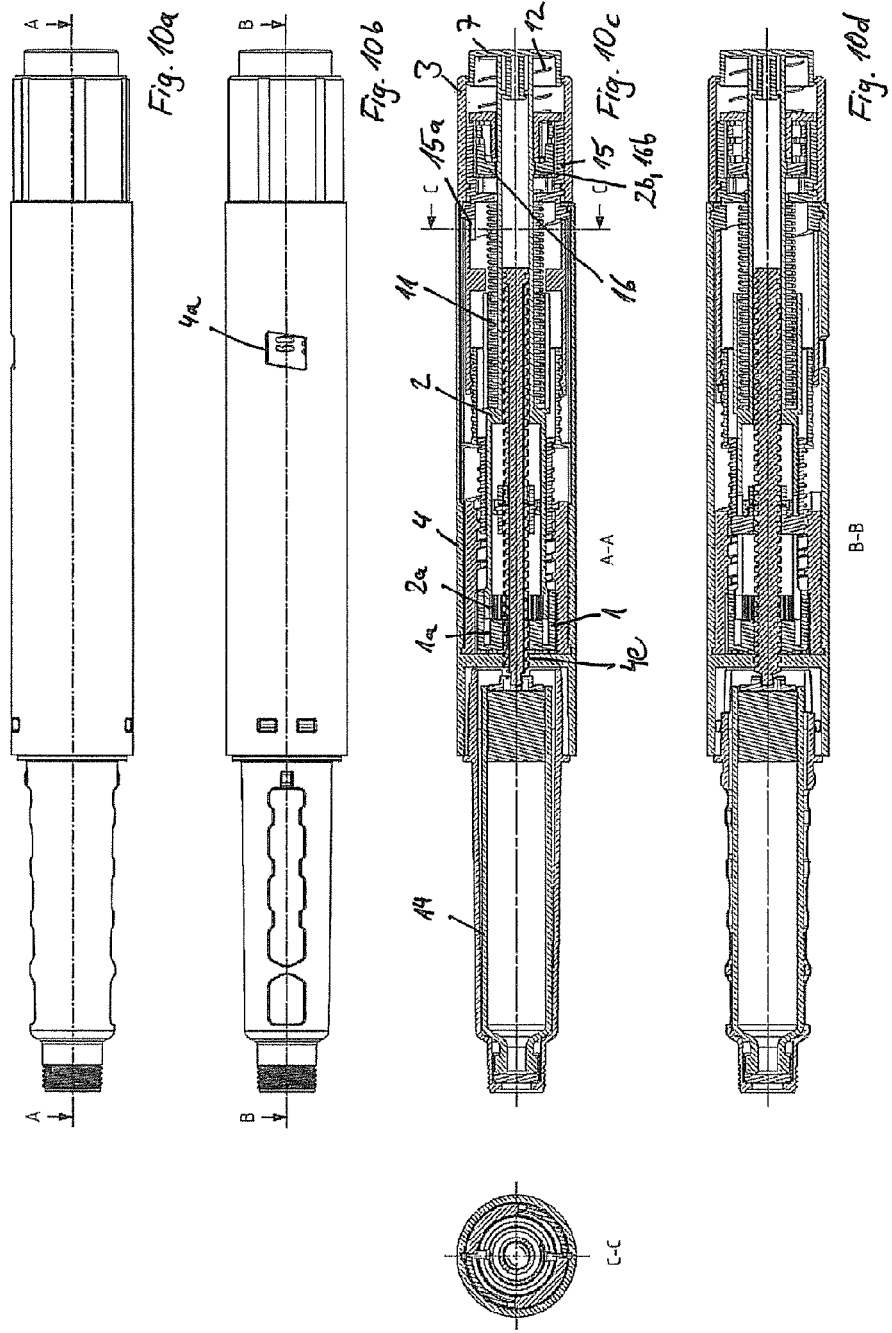

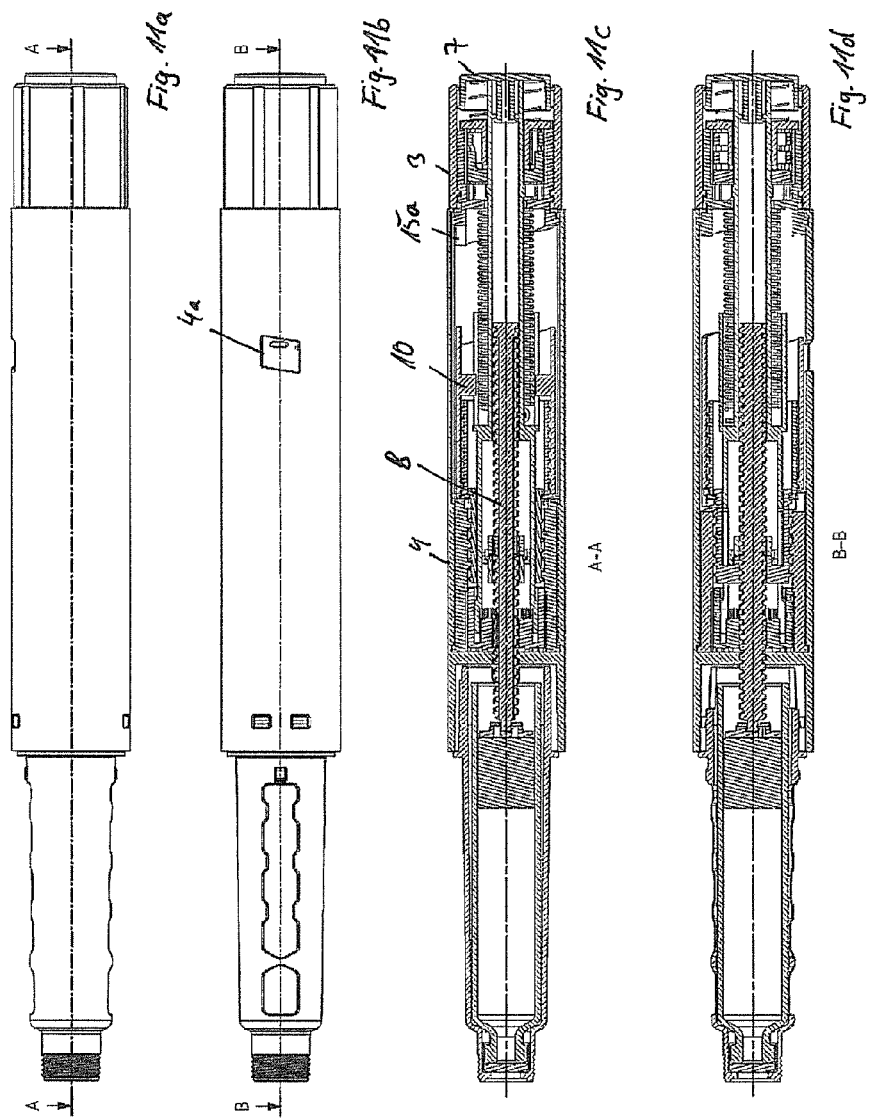

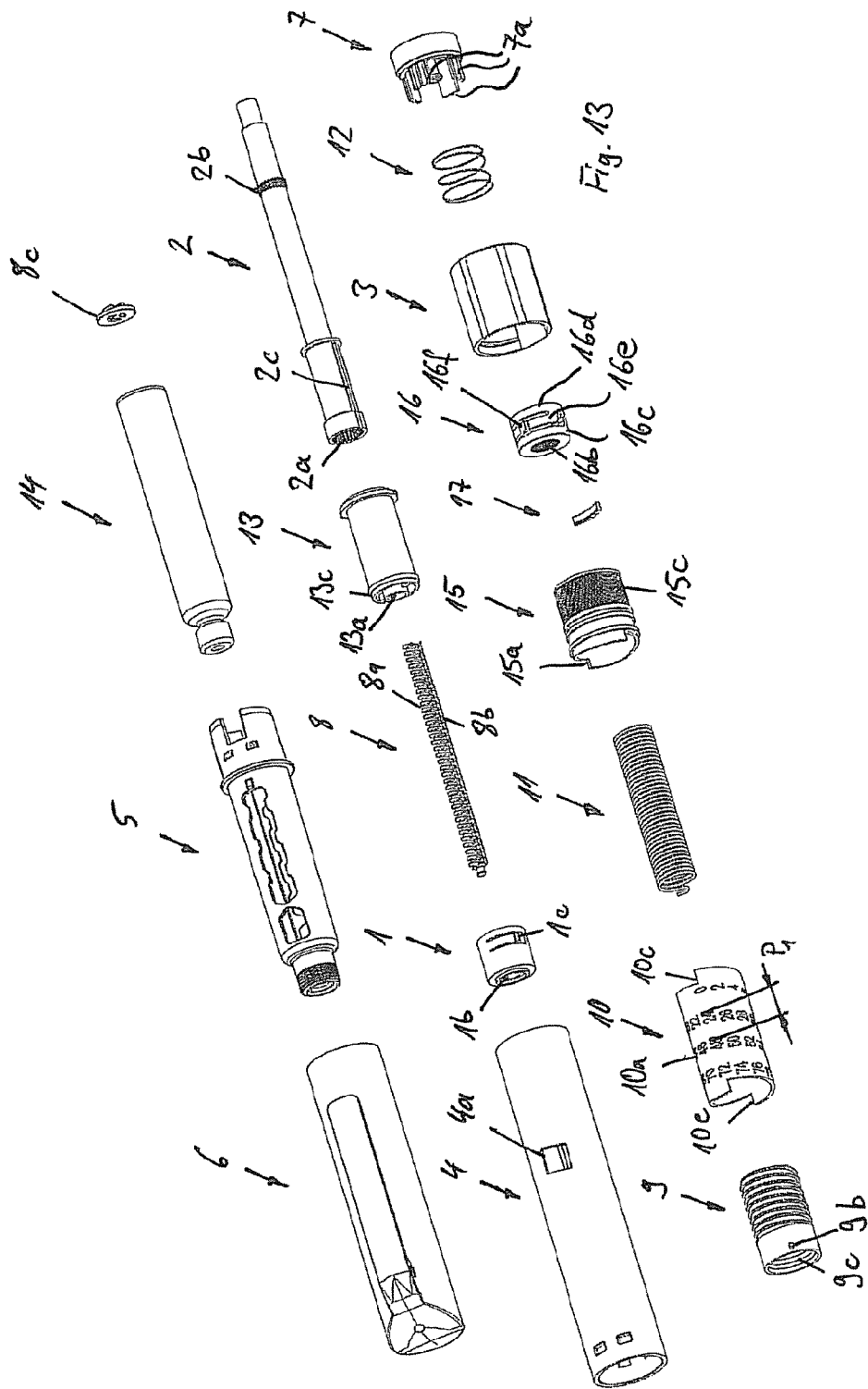

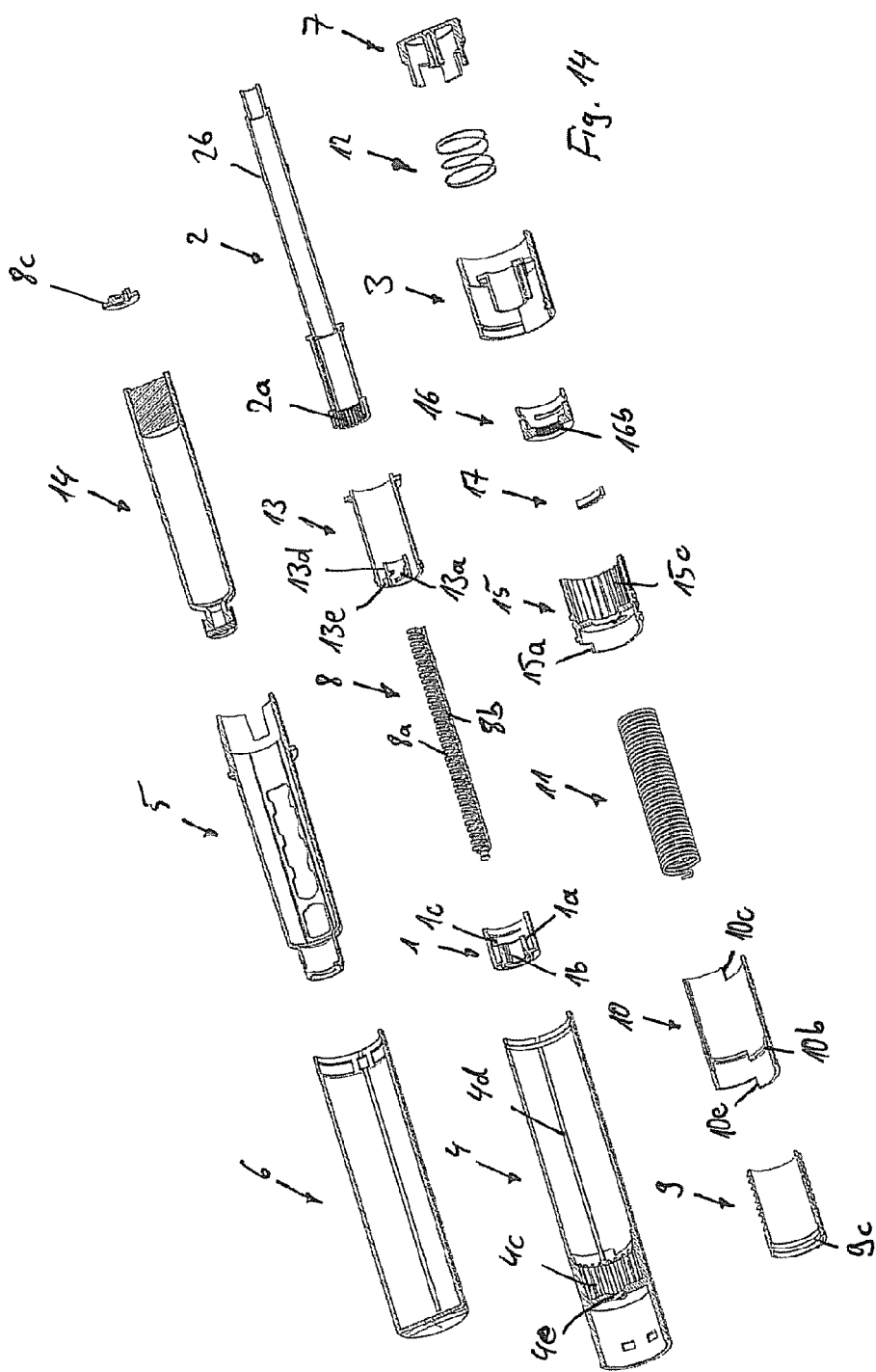

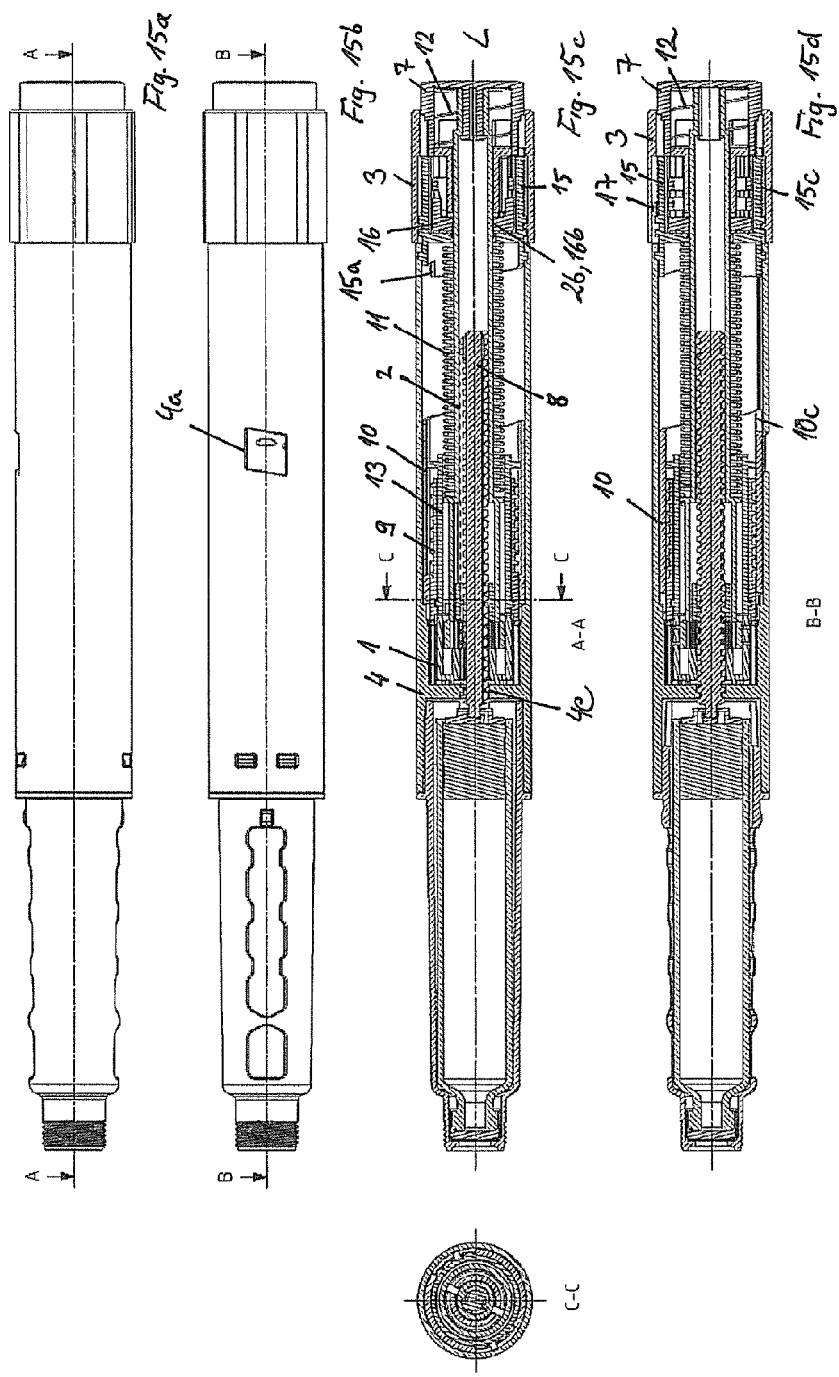

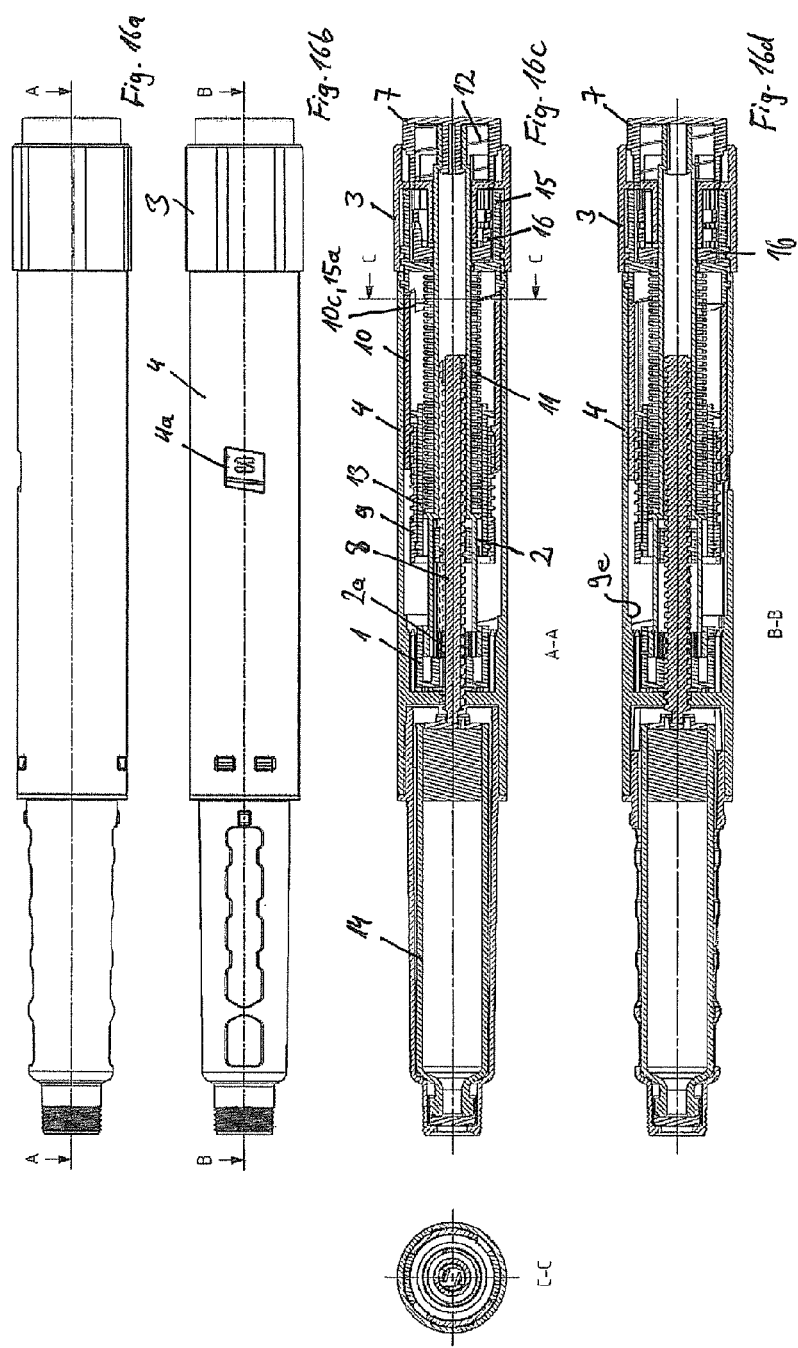

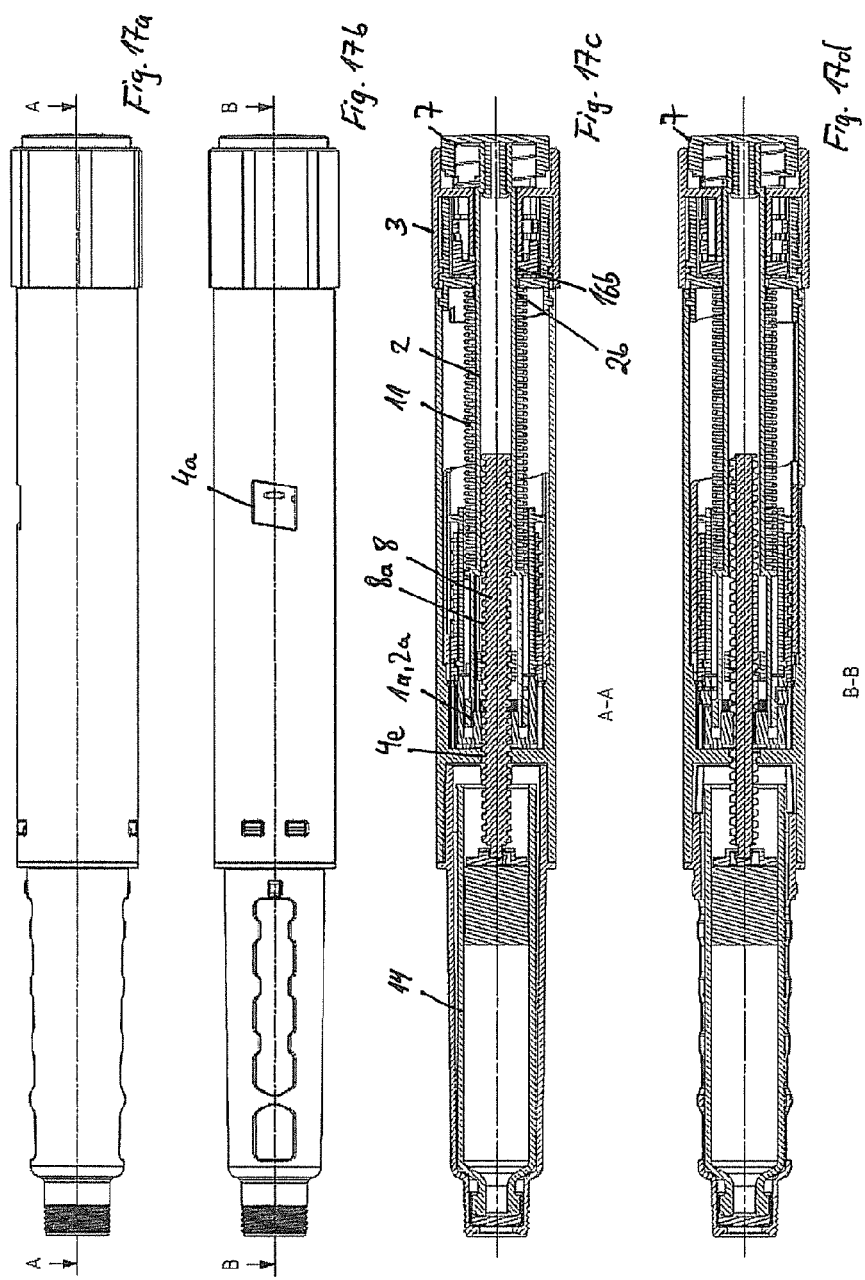

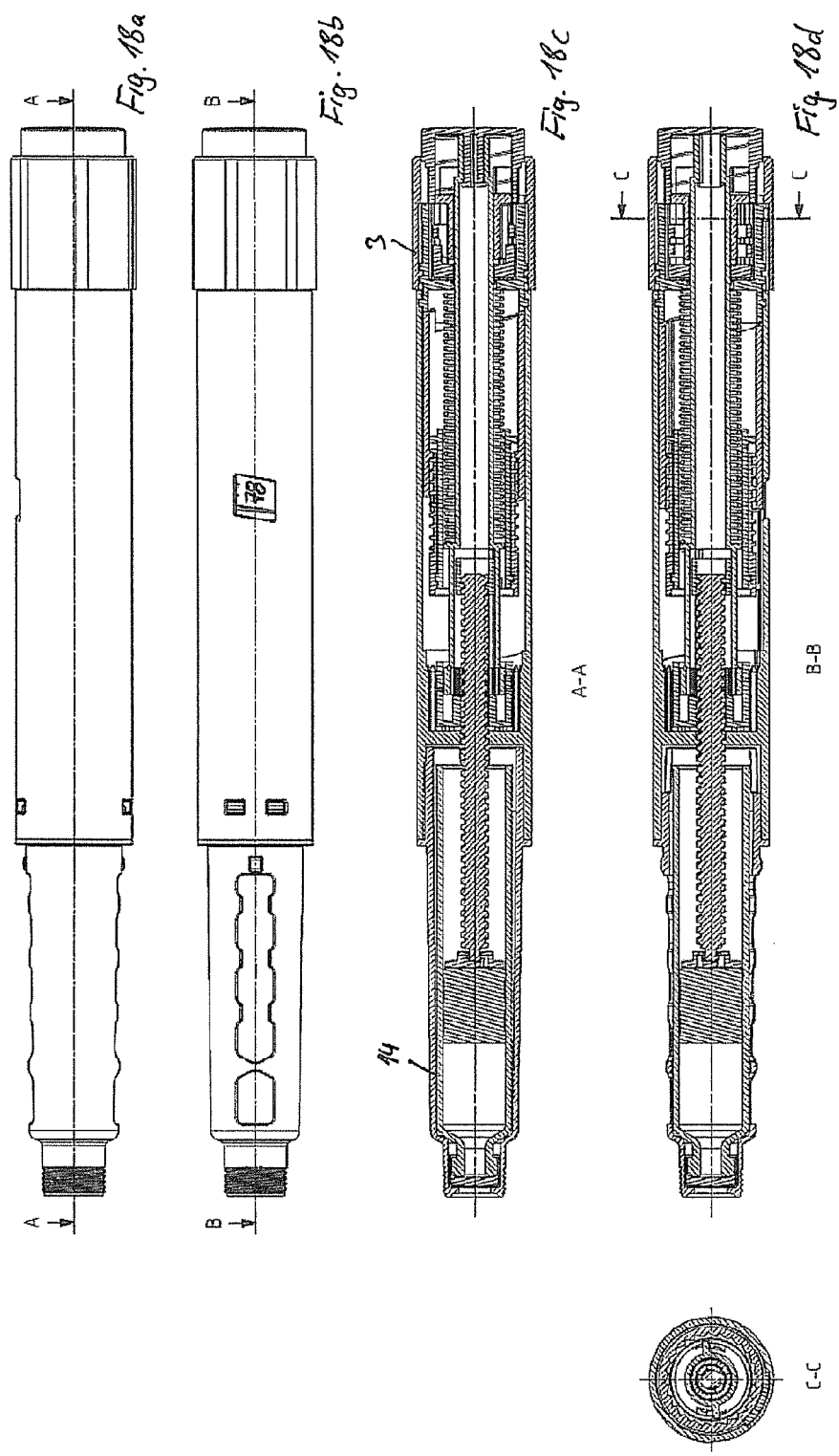

INJECTION DEVICE HAVING A HELICAL OR SPIRAL DOSAGE SCALE

CROSS-REFERENCE TO RELATED APPLICATIONS

This application is a Continuation of International Patent Application No. PCT/CH2013/000132 filed Jul. 17, 2013, which claims priority to European Patent Application No. 12 178 913.5 filed Aug. 1, 2012, the entire contents of each are incorporated herein by reference.

BACKGROUND

The invention relates to a driving and metering device for an injection device for administering a liquid product, particularly a medicine such as insulin. A product dose to be administered can be set and preferably dispensed with the driving and metering device, wherein these steps can be repeated multiple times. The invention thus also relates to an injection device having such a driving and metering device.

From the prior art, particularly WO 2009/105909 A1, an injection device is known that has a housing in which is arranged a dosage display sleeve with a helical scale arranged over the circumference thereof. A rotatable metering button that is axially fixed in relation to the housing is arranged at the rear end of the housing. By rotating the metering button, the dosage display drum is screwed along a thread formed on the housing. The thread has the same pitch as the helical scale on the circumference of the dosage display element.

WO 2005/046770 A1 describes an injection device having an adjusting element at the distal end thereof that is used for setting the injection dosage. The adjusting element further comprises a helical dosage scale. The adjusting element is in threaded engagement with the housing via a first thread and, via a second thread, with a slide that is rotationally fixed in relation to the housing but is axially movable. The thread for the threaded engagement with the housing has a pitch equal to that of the helical dosage scale, while the thread for the engagement with the slide has a smaller pitch than that of the dosage scale.

The devices known from the prior art are quite challenging in regard to assembly. In particular, it is necessary to bring the adjusting element into engagement with two threads of different pitches during assembly in WO 2005/046770 A1.

SUMMARY

One problem addressed herein is that of specifying a driving and metering device that is easy to assemble and therefore cost-effective to produce. The problem is solved with the metering and drive device as disclosed herein as well as disclosed advantageous refinements.

Disclosed implementations provide a drive mechanism, more particularly a driving and metering device, for an injection device for administering a liquid medicine or product. The driving and metering device advantageously has a housing. The housing may be sleeve-shaped and/or elongated in shape. The housing can extend along a longitudinal axis, for example.

The housing can optionally accommodate a product container or can itself constitute the product container. The housing can be in one or more parts. For example, the housing can form a proximal housing part that comprises or has the driving and metering device. The housing can additionally have a product container holder, which receives the product container such as a carpule and is connected to the housing or the proximal housing part. This connection can be such that the product container holder and the housing or the proximal housing part are non-detachable after connection, i.e., only detachable from one another by destroying connecting elements. Such a solution is particularly advantageous for single-use injection devices, which can be disposed of as a whole after the product contained in the product container has been completely dispensed. Alternatively, the product container holder can also be detachably connected to the housing, whereby it may be possible to use the driving and metering device several times if necessary, i.e., to replace an empty product container with a filled product container.

The housing is principally used in order to be gripped by the user of the device. In particular, the housing can have a substantially cylindrical shape. The housing can have an indication device, particularly a window, by means of which or through which the currently set dose can be read, preferably from a scale of a dose-setting element.

The driving and metering device comprises a dosage display element, over the circumference of which a dosage scale is arranged, and which can be arranged in the housing, for example. A helical or spiral dosage scale is arranged over the circumference of the preferably sleeve-like dosage display element. Such a dosage display element is conventionally referred to as a dosage display drum. The dosage scale can extend in a helical or spiral shape across the circumference, i.e., the dosage scale can cross the circumference of the dosage display element multiple times. The dosage scale preferably comprises a plurality of values, more particularly numerical values, which are arranged one after another and produce the dosage scale. The values can thus be arranged one alongside one another such that a helical or spiral dosage scale results. These are preferably numerical values that indicate the product dose to be dispensed in international units (IU).

The helical or spiral scale twists with a pitch, preferably a constant pitch, over the circumference of the dosage display element. By analogy to the thread pitch defined for the thread, the pitch of the dosage scale is understood to be the distance along the longitudinal axis that is traveled during one full rotation of the dosage display element. The advantages of a helical dosage scale are that the dosage display element can be rotated more than one revolution without the scale values repeating, whereby higher or more scale values can advantageously be represented.

The driving and metering device further comprises an indication device and a metering member that can be gripped by the user of the driving and metering device. In order to set the dosage, the dosage display element can be rotatable relative to the indication element and/or an actuating member about an axis of rotation corresponding to the aforementioned longitudinal axis by means of a rotation of the metering member. The preferably sleeve-like metering member can be arranged at the rear, or proximal, end of the housing or the driving and metering device. The metering member can be connected axially fixedly and rotatably to the housing or an element fixed in relation to the housing, or can be attached thereto.

The metering member can be constructed as a metering button and is optionally referred to as a dose-setting member. The metering member can preferably be gripped by the user (patient, physician, medical assistance personnel) of the driving and metering device and preferably constitutes an external, more particularly externally accessible, surface of the driving and metering device. To set the dosage to be dispensed or administered, the metering member is preferably gripped by the user and rotated relative to the housing, and in particular to the indication device, about an axis of rotation, which preferably corresponds to the longitudinal axis of the driving and metering device, which is designed in an elongated shape, for example. The metering member, preferably connected axially fixedly and rotatably to the housing, enables intuitive handling of the device by the user, who needs only to perform a rotational movement of the metering member to set a dosage.

A value of the dosage scale that corresponds to the set dose can be read by means of the indication device, which is preferably formed on the housing. The indication device can be a window, for example, which can be formed by an opening in the housing or by a transparent insert. Alternatively or optionally, the indication device can be an arrow or have an arrow, which marks the value of the dosage scale corresponding to the set dose in addition to the window. This is advantageous if a second value appears in the window, at least partially, in order to ensure an unambiguous choice of dosage, for example. The pointer can be a protrusion or an imprint or a notch or the like.

For intuitive operation, it is advantageous if, when the metering member is rotated by a given angle of rotation, the dosage display element is rotated by the same angle of rotation.

The driving and metering device can have an actuating member, in the form of an actuating button, for example. The actuating member can form an outer surface of the driving and metering device and/or can be accessible from the exterior. The actuating member can be formed on the proximal end, in particular the rear end, of the driving and metering device or can constitute this end. In this manner, the actuating member can advantageously be actuated, particularly pressed, with the thumb of the hand that is gripping the housing. The actuation can be ended by releasing the actuating member. "Actuating" is understood to mean the displacement of the actuating member into the driving and metering device, more particularly in the distal direction, which can effect the dispensing of a product. The actuating member is advantageously displaceable, in particular by an actuation stroke, relative to the metering member and in particular can be received by the metering member so as to be displaceable axially. The actuating member is preferably decoupled from the axial movement of the dosage display element relative to the metering member that is performed during dose-setting. In other words, the actuating member retains its position relative to the metering member along the axis of rotation when the metering member is rotated.

The actuating member can advantageously be displaceable, more particularly actuatable, against the force of at least one spring, particularly a return or coupling spring, whereby this at least one spring is cocked. By being released, this spring can reset the actuating member, more particularly displace it relative to the metering member, specifically in the proximal direction or out of the driving and metering device. The reset spring can be arranged between the actuating member and the metering member or can be supported thereon.

The driving and metering device further comprises a bearing element, with which the dosage display element is in a threaded engagement. The dosage display element has a thread that engages with a thread of the bearing element. For example, the bearing element can have an external thread and the dosage display element can have an internal thread, or vice versa. This engagement causes the dosage display element to be screwable relative to the bearing element. It is advantageous that the bearing element is rotationally fixedly connected to or engaged with the housing, it being preferred that the bearing element is axially movable relative to the housing. In particular, the bearing element can be displaced axially by turning the metering member.

The thread pitch of the housing element thread, and thus of the bearing element thread as well, is not equal to, more particularly is larger than or smaller than, the pitch of the helical scale. The different pitches make it possible to mount the bearing element on a part that carries out at least an axial movement along the longitudinal axis, wherein the dosage display element can advantageously forego a thread engaging with the housing. This facilitates the assembly of the driving and metering device and thus lowers the costs.

During dose-setting, or rotation of the metering member, the dosage display element carries out a rotational movement relative to the housing or the indication device—despite the different pitches—that is equal to the pitch of the dosage scale. This ensures that at least one scale value of the dosage scale can be properly read in the indication device. During rotation of the metering member, the part to which the bearing element is fixed, and which is rotatable and axially fixed relative to the bearing element, is preferably displaced along the longitudinal axis by an amount that is equal to the difference between the pitch of the dosage scale and the pitch of the threaded engagement between the bearing element and the dosage display element.

The threaded sleeve is preferably rotatable and axially fixed to the bearing element.

The threaded sleeve can have a thread, more particularly an internal thread, which engages with a thread, more particularly an external thread, of an advancement means such as a piston rod.

Alternatively or additionally, the threaded sleeve can have a thread, more particularly a second thread, which is preferably an external thread, the second thread engaging with an element fixed in relation to the housing, in particular with a thread of a part fixedly connected to the housing, or engaging directly with the housing itself. For a better distinction between the threads, the thread of the advancement member that engages with the thread of the threaded sleeve can be referred to as the first thread. The first thread and the second thread preferably have the same thread pitch.

The preferably elongated advancement member can be rotationally fixed relative to the housing or the indication device during dose-setting, whereby the threaded sleeve can be screwed along the thread of the advancement means. For example, the threaded sleeve is rotationally fixed to the advancement member, at least during dose-setting. The threaded sleeve can be indirectly, and in particular permanently, connected to the dosage display element for conjoint rotation therewith. The threaded sleeve can advantageously be connected to the dosage display element for conjoint rotation during dose-setting and dispensing of the product.

In order to ensure that the dosage scale performs the rotational movement in relation to the indication device with the pitch of the dosage scale, it is advantageous that the sum of the thread pitch of the dosage display element thread engaging with the thread of the bearing element and of the thread pitch of the first thread engaging with the thread of the advancement means is equal to the pitch of the helical dosage display element scale. This ensures that the threaded sleeve, and thus the bearing element as well, are displaced by the distance corresponding to the above-mentioned difference when the metering member is rotated.

Alternatively or additionally, the sum of the thread pitch of the dosage display element thread engaging with the bearing element thread and of the thread pitch of the threaded sleeve thread engaging with the thread stationary relative to the housing is equal to the pitch of the helical dosage display element scale. This achieves the same effect.

In preferred embodiments, the threaded sleeve can be rotatable relative to the advancement member during dose-setting and rotationally fixed relative to the advancement member during dispensing of the product. In preferred embodiments, the dosage display element can be rotationally fixed to and axially displaceable with a clutch member, which is rotatable relative to the indication device during dose-setting and preferably during dispensing of the product.

The advancement member, preferably constructed as a piston rod, has an external thread, which can preferably be overlapped by a longitudinal guide, particularly a flattening or a longitudinal groove. For example, the thread of the advancement member can be in a threaded engagement with a thread of the housing or an element fixed in relation to the housing, whereby a rotation of the advancement member about the longitudinal axis causes the advancement member to be moved, in particular screwed, along the longitudinal axis. During dispensing of the product, the advancement member is rotated in a direction that causes the advancement member to be displaced into the product container and thereby displaces the piston in the product container.

In preferred embodiments, the driving and metering device comprises a clutch, in particular a first clutch, which is disengaged when the actuating member is not actuated, and is engaged when the actuating member has been actuated or which is engaged by actuating the actuating member. The engaged clutch connects the clutch member and the advancement member for conjoint rotation. The clutch member is rotatable relative to the advancement member when the clutch is disengaged.

The clutch can comprise a first clutch structure and a second clutch structure, which engage with one another when the clutch is engaged and are disengaged when the clutch is disengaged. The clutch can be a claw clutch for example. The first clutch structure and the second clutch structure can each have toothing, wherein the toothings can engage with one another to form a rotationally fixed connection. For example, the first clutch structure is external toothing and the second clutch structure is internal toothing, or vice versa. The first clutch structure can be arranged on the clutch member, while the second clutch structure can be formed on a rotation element.

The rotation element can have a sleeve-like shape and can be connected rotationally fixedly but axially movably to the advancement member. For this purpose, the rotation element can have a ridge, which engages non-rotatably in the longitudinal guide, more particularly the groove or the flattened portion, of the advancement member. The rotation element can have a resiliently arranged engagement member, which can be constructed in the form of a cam on an arm, for example. The engagement member of the rotation element can engage with internal toothing of the housing or of an element fixed in relation to the housing. The rotation element can function as a unidirectional clutch, wherein a rotation of the rotation member, and thus of the advancement member (e.g., piston rod) as well, is possible only in the direction that effects a dispensing movement of the advancement member, and is blocked in the opposite direction. Such a unidirectional clutch can also be referred to as a ratchet.

If the actuating member has been actuated, a rotation of the clutch member causes the rotation element to be rotated relative to the housing or the indication device.

Alternatively or additionally, the driving and metering device comprises a clutch, in particular a second clutch, which is engaged when the actuating member is not actuated, and is disengaged when the actuating member has been actuated or which is disengaged by actuating the actuating member. The engaged second clutch can connect the metering member and the clutch member rotationally fixedly at least in one rotational direction, preferably in both directions, in particular apart from certain elasticities. The clutch member can be rotatable relative to the metering member when the second clutch is disengaged. The second clutch can have a third and a fourth clutch structure which are disengaged when the second clutch is disengaged, and are rotationally fixedly engaged when the second clutch is engaged. The second clutch can be a claw clutch. The third clutch structure and the fourth clutch structure can each have toothing, wherein the toothings can engage with one another to form a rotationally fixed coupling. For example, the third clutch structure is external toothing and the fourth clutch structure is internal toothing, or vice versa. The third clutch structure can be formed on the clutch member, for example, and the fourth clutch structure on the metering member or on a coupling element, which can be part of a blocking device.

It is particularly advantageous if the clutch member is rotationally fixedly coupled to the rotation element and the rotation element is rotationally fixedly coupled to the metering member by means of the second clutch while the actuating member is being pressed for actuation in relation to the housing. This ensures that the clutch member is coupled securely to the rotation element when the clutch member has been released for a rotation relative to the housing. In other words, there is an intermediate position between the completely actuated and the non-actuated position of the actuating member, in which the rotation element is both coupled rotationally fixedly to the metering member and also rotationally fixedly to the dosage display element.

The driving and metering device preferably comprises a clutch spring that tensions the first clutch in the disengaged position and/or the second clutch in the engaged position when the actuating member has not been actuated. The clutch spring can be the aforementioned coupling spring or return spring, which is cocked by actuating the actuating member.

The sleeve-like clutch member can preferably be connected permanently in a rotationally fixed manner, and preferably axially movably, to the threaded sleeve and/or the dosage display element. This has the effect that the dosage display device displays the dosage that can be set by rotating the metering member and that the dosage display element counts back down to the value zero when the actuating member has been actuated.

The driving and metering device further comprises a drive spring, which is cocked, or can be cocked by rotating the metering member, and drives the advancement member during dispensing of the product. The energy required for the back-rotation of the dosage display element or/and the movement of the advancement member in the distal direction can be exerted automatically, more particularly by means of a spring contained in the driving and metering device, in particular a dispensing spring, in which the required energy is or can be stored. For example, the spring energy stored in the dispensing spring can be output upon actuation of the actuating member to the dosage display element and/or the advancement member, so that the dosage display element is rotated back and the advancement member is moved in the distal direction. The dispensing spring is preferably coupled to the metering member, particularly via a releasable coupling, in such a manner that a rotation of the metering member during dose-setting, more particularly during increasing of the dosage or rotation in the first rotational direction, cocks the dispensing spring. The dispensing spring can then store the energy required for the set dose.

A rotation of the metering member in a first rotational direction, which causes a reduction of the dosage, can cause the dispensing spring to be relaxed or not relaxed. If the dispensing spring is to be relaxed upon rotation of the metering member in the first rotational direction, one end of the spring can be rotationally fixedly coupled in both rotational directions to the metering member, more particularly by the clutch. If the dispensing spring is not to be relaxed upon rotation of the metering member in the first rotation direction, it is advantageous to arrange a unidirectional clutch, more particularly a ratchet, kinematically between the metering member and the spring, in addition to the aforesaid clutch, wherein the ratchet transfers the rotation of the metering member in the second direction to the dispensing spring and does not transfer the rotation of the metering member in the first rotational direction to the dispensing spring.

For example, the dispensing spring can be a helical or spiral spring acting as a torsion spring. The dispensing spring can be rotationally fixedly supported at one end on the clutch member and at the other end on the housing or an element fixed in relation to the housing.

In preferred embodiments, the driving and metering device can have a releasable blocking device, which is inserted between the metering member and the clutch member, and in particular the housing, in such a manner that torque exerted by the drive spring onto the clutch member is directed into the housing so that the clutch member is secured against rotation relative to the housing, wherein this rotational inhibition of the clutch member can be released by rotation of the metering member, so that the clutch member is rotatable relative to the housing in a first and preferably also in a second direction.

In addition, the driving and metering device can comprise a mechanism for preventing the setting of a dosage that exceeds the quantity of a medication in the product container. In particular, this mechanism can block rotation of the metering member in a direction that would cause an increase of the dosage, more particularly even if the maximum stop of the dosage display element and the maximum-dose mating stop are not yet engaged or if a dosage is displayed in the indication device that is smaller than the maximum product dose that can be set. The mechanism thus prevents setting a dosage that exceeds the remaining dispensable amount of product contained in the product container, which reduces the danger of misuse of the driving and metering device. The mechanism can have a limiter, for example, which is mounted between two parts, one of which rotates relative to the other during dose-setting and does not rotate upon actuation, i.e., dosage dispensing; for example, the limiter can be arranged between the dose-setting member, which can be designed in particular as a dose-setting button or dose-setting sleeve, and the housing or an element fixed relative to the housing. The limiter, the dose-setting element and the housing can be coupled to one another in such a manner that a relative rotation, particularly during dose-setting, between the dose-setting element and the housing causes the limiter to move to a stop position in which the limiter prevents setting a dosage that exceeds the amount of a product in the product container. Examples of appropriately suitable limiters are disclosed in WO 2010/49209 or in WO 01/19434 A1, particularly in FIG. 3 thereof. For example, the limiter can have an internal thread that is engaged with an external thread of the housing. In particular, the limiter can have a longitudinal guide on its outer side by which it is engaged with the dose-setting element such that the dose-setting element is rotationally fixed relative to the limiter. Alternatively, the housing can have the longitudinal guide for the limiter, so that the limiter is rotationally fixed relative to the housing and the limiter can have a thread, particularly an external thread, that engages with a thread, particularly an internal thread, of the dose-setting element.

The stopping position is defined by a limit stop for the limiter, wherein the limit stop can be formed by the housing or the dose-setting element or a means fixed relative to the housing at least axially or in the circumferential direction. If the limiter and the limit stop are in contact, the rotation of the dose-setting element in the direction that would cause an increase of the dosage, e.g., the second rotational direction, is no longer possible or is blocked.

In an alternative embodiment for such a mechanism, the limiter can be formed by the threaded sleeve, wherein the stopping position is defined by a stop on the advancement member, particularly at the rear end or proximal end of the advancement member. This stop can be a stop acting in the axial direction or a stop acting in a circumferential direction.

BRIEF DESCRIPTION OF THE DRAWINGS

FIG. 2 shows the representation from FIG. 1, with the individual parts represented in section.

FIGS. 3a-3d show various views of an injection device composed of the individual parts from FIGS. 1 and 2, in an initial or delivery state.

FIGS. 4a-4d show the views of the device from FIGS. 3a-3d, with a maximum set product dose.

FIGS. 5a-5d show the views of the device from FIGS. 3a-3d, after dispensing of the set product dose.

FIGS. 6a-6d show the views of the device from FIGS. 3a-3d, in a state in which the dispensable product dose contained in the product container is less than the maximum dosage that can be set with the device.

FIG. 7 shows an exploded view of the individual parts of an injection device having a driving and metering device according to a second embodiment.

FIG. 8 shows the representation from FIG. 7, with the individual parts represented in section.

FIGS. 9a-9d show various views of an injection device composed of the individual parts from FIGS. 7 and 8 in an initial or delivery state.

FIGS. 10a-10d show the views of the device from FIGS. 9a-9d, with a maximum set product dose.

FIGS. 11a-11d show the views of the device from FIGS. 9a-9d, after dispensing of the set product dose.

FIG. 13 shows an exploded view of an injection device having a driving and metering device according to a third embodiment.

FIG. 14 shows the representation from FIG. 13, with the individual parts represented in section.

FIGS. 15a-15d show various views of an injection device composed of the individual parts from FIGS. 13 and 14 in an initial or delivery state.

FIGS. 16a-16d show the views of the device from FIGS. 15a-15d, with a maximum set product dose.

FIGS. 17a-17d show the views of the device from FIGS. 15a-15d, after dispensing of the set product dose.

FIGS. 18a-18d show the views of the device from FIGS. 15a-15d, in a state in which the dispensable product dose contained in the product container is less than the maximum dose that can be set with the device.

DETAILED DESCRIPTION

Figure 1:
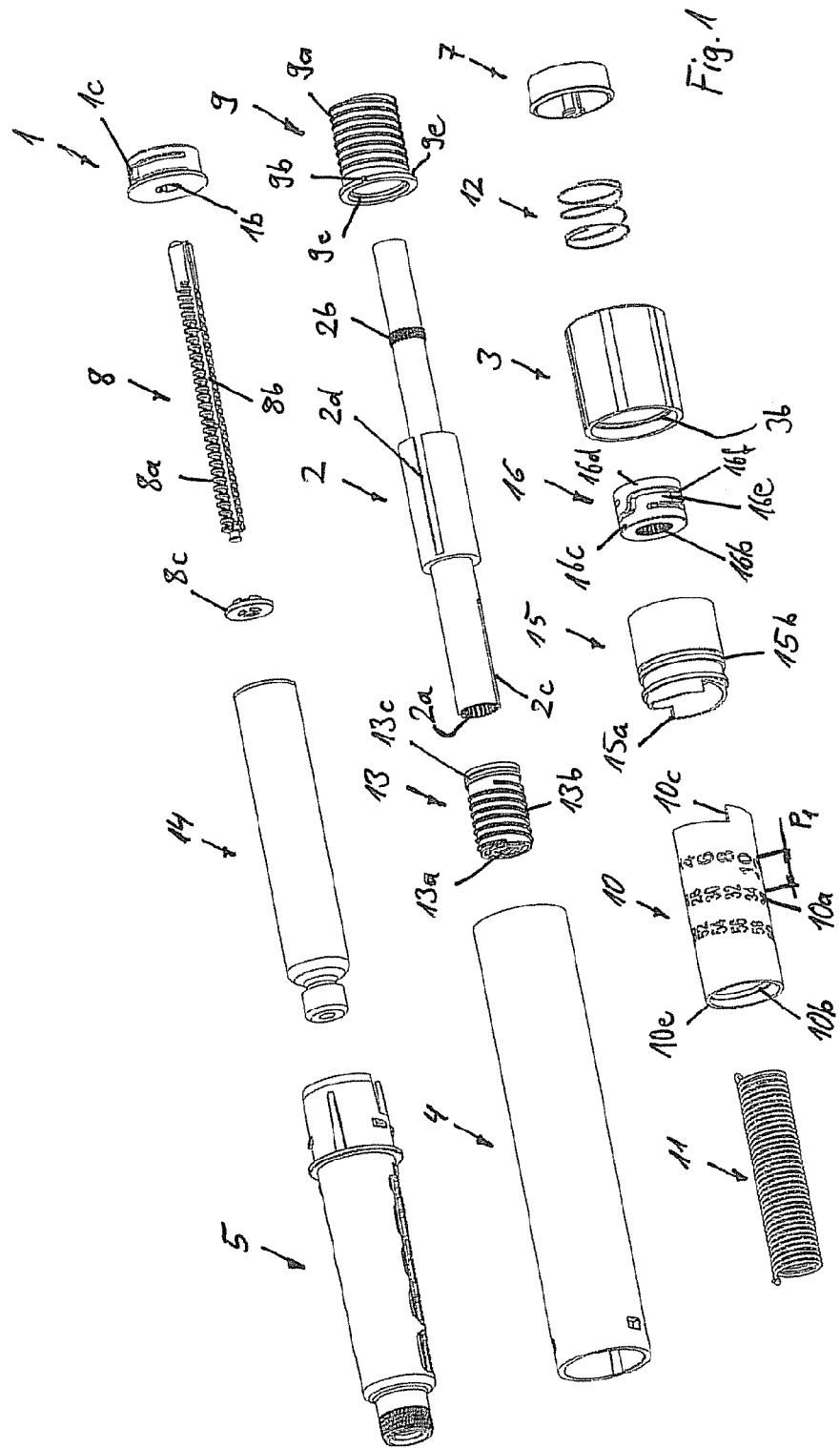
FIG. 1 shows an exploded view of individual parts of an injection device having a driving and metering device according to a first embodiment.
Figure 12A:
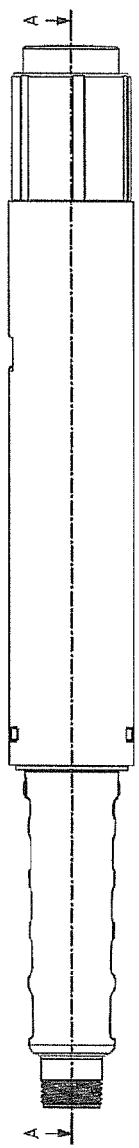
FIGS. 12a-12d show the views of the device from FIGS. 9a-9d, in a state in which the dispensable product dose contained in the product container is less than the maximum dose that can be set with the device.
Figure 12B:
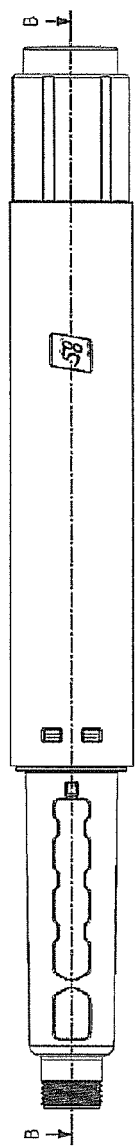
Figure 12C:
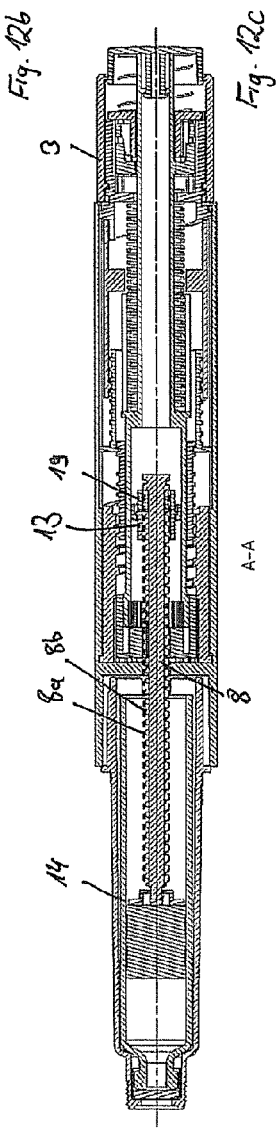
Figure 12D:
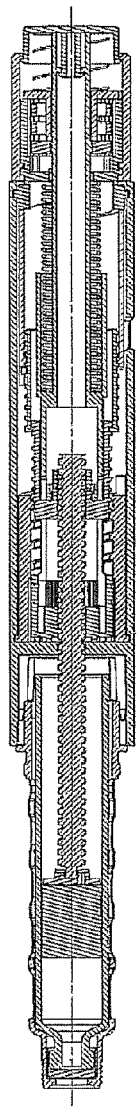

First, the common features among the first, second and third embodiments will be described. Then the special features of each embodiment will be described.

The embodiments shown in the figures have a sleeve-like housing 4, in which a window-like opening for forming an indication device 4a is arranged. At the distal, i.e., front, end of the housing 4, a product container holder 5 is mounted, preferably non-detachably, more particularly snapped in, which holds a product container 14 in the form of a carpule. The carpule has a cylindrical housing, in which a piston is displaceably arranged. At the distal end, the carpule has a septum that can be punctured by a needle. The product to be administered is located between the septum and the piston. The product is forced out of the product container 14 by displacing the piston in the direction of the septum. A thread or a bayonet mount, to which the needle can be affixed, is formed at the proximal end of the product container holder 5. A cap 6 can be removably pushed onto the product container holder 5.

At the proximal, i.e., rear, end of the housing 4, is arranged a metering member 3, rotatable relative to the housing 4 and forming an outer surface of the device; the metering member can be gripped by the user of the device and is rotatable relative to the housing 4. A rotation of the metering member 3 in a first rotational direction causes a reduction of the dosage, while a rotation of the metering member in a second rotational direction causes an increase of the dosage. The metering member 3 is connected axially fixedly to the housing 4. A housing insert 15, mounted secured against rotation and axial movement on the housing 4, is fixed in relation to the housing and can therefore be counted as part of the housing 4. The housing insert 15 has an annular groove 15b, into which an annular ridge 3b on the inner circumference of the metering member 3 snaps, whereby the metering member 3 is connected rotatably and axially fixedly to the housing insert 15. The housing insert 15 is sleeve-shaped.

At the distal end of the housing insert 15 is formed a maximum-dose mating stop 15a for a maximum-dose stop 10c of a dosage display element 10.

The housing insert 15 has toothing 15c extending across the inner circumference. The housing insert 15 surrounds a one-piece coupling element 16, which is preferably produced from plastic and/or is an injection molded part. The coupling element 16 has a first section 16c and a second section 16d. The first section 16c is connected to the second section 16d via an elastically deformable intermediate section 16e. The intermediate section 16e transitions at one end into the first section 16c and at the other into the second section 16d. The intermediate section 16e extends in the first rotational direction from the first section 16c, and in the direction opposite the first rotational direction, i.e. in the second rotational direction, from the second section 16d. The intermediate section 16e is preferably elongated and extends over at least a part of the circumference of the coupling element 16. The coupling element 16 has two such intermediate sections 16e, which are, in particular, arranged offset by 180° across the circumference.

The intermediate section or sections 16e each have a respective engagement member 16f, which engages with the toothing 15c of the sleeve 15. In particular, the engagement member 16f is a tooth or cam projecting radially outward from the circumference of the coupling element 16.

The engagement member 16f has a first tooth flank pointing in the first rotational direction and a second tooth flank pointing in the second rotational direction. The first and second tooth flanks are arranged with different slopes, so that the engagement member 16f has a sawtooth shape. The first flank is preferably arranged to be steeper than the second flank.

The engagement member 16f is preferably arranged between the ends of the intermediate section 16e, preferably in the center.

The toothing 15c has a plurality of teeth distributed across the circumference. One or more teeth, in particular each of these teeth, can be formed in a sawtooth shape, for example. They can have a first flank pointing in the circumferential direction and a second flank pointing opposite the first flank in the circumferential direction, wherein the first flank is formed more steeply than the second flank. The first flank preferably forms a mating flank for the first flank of the engagement member 16f.

A torque application means, in this example, a spring 11 designed as a coil spring, functioning as a torsion spring and serving as a drive spring, is supported at one end, in particular the distal end, on a clutch member 2 rotatable relative to the housing 4, and is fixed in relation to the housing, in particular on the housing insert 15 at the other end, in particular the proximal end. Rotation of the clutch member 2 in the second rotational direction causes cocking of the spring 11, while rotation in the second direction causes relaxation of the spring 11. The clutch member 2 is preferably connected substantially rotationally fixedly via a releasable second clutch 2b, 16b to the metering member 3. The clutch member 2 has a clutch structure 2b for forming the second clutch 2b, 16b. The first section 16c of the coupling element 16 has a clutch structure 16b for forming the second clutch 2b, 16b, and said clutch structure being in a rotationally fixed engagement with the clutch structure 2b when the second clutch 2b, 16b is engaged.

In the first variant, the metering member 3 can be connected to the second section 16d of the coupling element 16 permanently or rotationally fixedly in both rotational directions. For the rotationally fixed connection, the second section 16d has on its inner circumference a groove 16a, with which a protrusion 3a of the metering member 3 engages. A stop 16g, against which a mating stop of the metering member 3, which can be formed by the rib-like protrusion 3a, is pressed when the metering member 3 is rotated in the second rotational direction, can optionally be formed on the first section 16c or the intermediate section 16e, more particularly between the engagement member 16f and the first section 16c, or where the intermediate section 16e transitions into the first section 16c. Thereby the torque acting on the metering member 3 is transmitted to the first section 16c, without having to pass across the entire intermediate section 16e. Thereby the coupling element 16 can be rotated even more easily in the second rotational direction relative to the toothing 15c.

In a second variation, the metering member 3 can be connected rotationally fixedly in the first direction to the second section 16d of the coupling element 16, and rotationally fixedly in the second rotational direction to the first section 16c or the connecting section 16e. For example, the metering member 3 can be rotatable relative to the second section 16d, more particularly to a limited extent such as a few degrees. For this connection, the second section 16d has, on its inner circumference, a stop 16a, against which a mating stop, in particular a protrusion or the longitudinal ridge 3a of the metering member 3, strikes in the first rotational direction. In the region of the connecting point to the first section 16c, the intermediate section 16e further comprises a stop 16g, against which a mating stop, in particular, the protrusion or the longitudinal ridge 3a, strikes in the second rotational direction.

These two variants have the effect that torque exerted by the metering member 3 onto the coupling element 16 runs over the entire connecting section 16e when the metering member 3 is rotated in the first rotational direction, so that the connecting section 16e can deform elastically. They have the additional effect that torque exerted by the metering member 3 onto the coupling element 16 is introduced on or into the first section 16d, without having to run across the entire connecting section 16e, when the metering member 3 is rotated in the first rotational direction.

It is true in general that the torque application means, in particular the spring 11, applies a torque directed about the longitudinal axis L in the first direction to the first section 16c of the coupling element 16. The level of the torque depends on how strongly the spring 11, particularly the torsion spring, is cocked rotationally. The engagement member 16f is pressed by the torque acting in the first rotational direction into the toothing 15c, so that a rotation of the coupling element 16 in the first direction relative to the housing insert 15 is blocked. In order for the engagement member 16f to be pressed securely into the toothing 15c even more securely, it is particularly advantageous that the intermediate section 16e extends circumferentially from the first section 16c in the first rotational direction. As an alternative or additional measure, the first flank of the engagement member 16f and the first flank of one of the teeth of the toothing 15c are matched to one another such that self-locking occurs between the engagement member 16f and the toothing 15c, i.e., the engagement member 16f is not pressed out of the toothing 15c even under a very high torque. The flanks can be matched to one another such that the engagement member 16f is pulled into engagement with the toothing 15c.

The second section 16d of the coupling element 16 can be elastically twisted relative to the first section 16c in the first rotational direction about the longitudinal axis L, more particularly by means of rotation of the metering member 3 in the first rotational direction. The ability to twist is provided by the elastic intermediate section 16e. Due to the torsion of the second section 16d relative to the first section 16c, the engagement of the engagement member 16f with the toothing 15c that locks rotation in the first rotational direction is released. The engagement member 16f is deflected inward slightly by the torsion, i.e. toward the axis of rotation L, so that the engagement member 16f is released from the rotationally fixed engagement. This enables a rotation of the coupling element 16 in the first direction relative to the sleeve 15. The engagement member 16f will therefore snap over the tooth in the toothing 15c with which it was engaged and will engage with the next tooth, more particularly the immediately adjacent tooth. Therefore the coupling element 16 can rotate in the first rotational direction relative to the housing insert 15 incrementally or by an angular increment corresponding to the tooth pitch of the toothing 15c.

Increasing the dosage and reducing the dosage can thus advantageously be enabled with a simply designed component, namely, the sleeve-like coupling element 16, and the relaxation of the spring 11 can be prevented.

By rotating the dosing member 3 in a second rotational direction, the engagement member 16f is locked via the teeth of the toothing 15c. The spring 11 is tensioned by the engaged clutch 2b, 16b.

In order to obtain the desired elasticity of the intermediate section 16e, the intermediate section 16e can have a different wall thickness than the first and/or second sections 16c, 16d. In the example shown, the wall thickness of the intermediate section 16e is less than the thickness of the first section 16c.

An actuating member 7 designed as an actuating button arranged at the proximal end of the driving and metering device can be pressed, in particular in the distal direction, by the user in order to dispense the product. The actuating member 7 is arranged in relation to the metering member 3 such that it does not change its axial position during dose-setting. In particular, the actuating member 7 is arranged in the metering member 3 so as to be displaceable by an actuation stroke length. A clutch spring or reset spring 12, formed as a coil spring and functioning as a compression spring, acts between the metering member 3 and the actuating member 7. The spring 12 is supported on the metering member 3 and the actuating member 7. The actuating member 7 constitutes the proximal end of the driving and metering device.

The actuating member 7 is connected at least axially fixedly, and preferably rotationally fixedly to the metering member 3 and is axially fixedly connected to the proximal end of the clutch member 2, more particularly snapped onto the clutch member. The actuating member 7 can be shifted back and forth between an actuated position and a non-actuated position.

The driving and metering device has an advancement member 8 in the form of a piston rod, at the distal end of which a flange 8c is arranged or fastened. The advancement member 8 acts on the piston of the product container 14 or preferably comes into contact with the piston. The advancement member 8 has an external thread 8a, which is overlaid by a groove 8b that extends in the longitudinal direction of the elongated advancement member 8.

The advancement member 8 is surrounded by a rotation element 1, which is preferably sleeve-like and is axially and rotationally fixed in relation to the advancement member 8. The rotation element 1 has a ridge 1b, which engages with the groove 8b to form the rotationally fixed and axially movable connection. On the periphery of the rotational element 1, it has a cam-like engagement member 1c that is resiliently arranged on a spring arm and is in threaded engagement with internal toothing 4c fixed relative to the housing and in particular formed by the housing 4.

The thread of the advancement member 8 is in a threaded engagement with an internal thread 13a of a threaded sleeve 13, such that the threaded sleeve 13 can be screwed along the advancement member 8. The threaded sleeve 13 is connected rotationally fixedly and axially movably to the clutch member 2, so that the clutch member 2 rotates conjointly with the threaded sleeve 13. For this purpose, an internal sleeve 13d, which is connected via at least one, preferably two or more, spoke-like webs 13e to the interior circumference of the threaded sleeve 13, can be formed in the threaded sleeve 13. The at least one web 13e reaches through at least one axially extending guide slot 2c of the clutch sleeve 2, preferably two or more respective guiding slots, thus realizing the rotationally fixed connection to the latter and an axial movability, preferably for the actuating or coupling stroke.

The threaded sleeve 13 is rotatably and axially fixedly mounted on a bearing element 9. For this purpose, the threaded sleeve 13 can have an annular groove 13c, for example, with which the bearing element 9 engages via an annular ridge 9c. The bearing element 9 is preferably rotationally fixed and axially movable relative to the housing 4. For the rotationally fixed and axially movable connection to the housing 4, the bearing element 9 engages, in particular by means of a protrusion 9b, with a groove 4d that extends along the longitudinal axis L.

The bearing element 9 has an external thread 9a that is in a threaded engagement with an internal thread 10b of the dosage display element 10 constructed as a dosage display drum. Therefore the dosage display element 10 can be screwed along the bearing element 9.

The dosage display element 10 has a spiral or helical dosage scale 10a that turns multiple times around the surface of the sleeve, the dosage scale being formed from a plurality of concatenated dosage values, indicated in particular in international units (IU). As is recognizable in FIGS. 1, 7 and 13, the dosage scale 10a can have dosage values that can be set from 0 to 60 or 80 IU, in increments of one or two steps. The product dose to be dispensed can be set by rotating the metering member 3 relative to the housing 4 or the indication device 4a, wherein the corresponding dosage value can be read at the indication device 4a or appears in the indication device 4a.

In particular, the dosage display element 10 is permanently rotationally fixed and axially movable in relation to the clutch member 2.

The clutch member 2 is rotationally fixedly connected to the rotation element 1, in particular by means of a first clutch 1a, 2a. For this purpose, the clutch member 2 has at the distal end thereof, a clutch structure 2a in the form of inner toothing. The rotation element 1 has a clutch structure 1a in the form of external toothing. If the actuating member 7 has not been actuated, the first clutch 1a, 2a is disengaged and the second clutch 2b, 16b is engaged, so that the clutch member 2 is rotatable relative to the rotation element 1 and/or to the advancement member 8, the metering member 3 being substantially rotationally fixed to the clutch member 2, apart from a certain elasticity of the clutch member 16. If the actuating member 7 has been actuated, in particular completely actuated, the first clutch 1a, 2a is engaged whereby the clutch member 2 is rotationally fixed relative to the rotation element 1 and/or the advance member 8, and the second clutch 2b, 16b is disengaged, whereby the clutch member 2 is rotatable relative to the metering member 3 and/or the housing 4. Between the non-actuated and the completely actuated position of the actuating member 7, there is an intermediate position, in which the first clutch 1a, 2a and the second clutch 2b, 16b are engaged. This advantageously prevents the clutch member 2 from being released for rotation relative to the housing 4 when the first clutch 1a, 2a has not yet been completely engaged. This would lead to a malfunction of the driving and metering device.

As soon as the second clutch 2b, 16b has been disengaged, the preloaded spring 11 can rotate the clutch member 2 and, via the engaged first clutch 1a, 2a, the rotation element 1 and the advancement member 8 relative to the housing 4, whereby the advancement member 8 is displaced in the dispensing direction, i.e., in the direction of the piston, and dispenses the set dose.

For dose-setting, i.e., with a non-actuated actuating member 7, the clutch member 2 is rotationally decoupled from the advancement member 8, so that metering movements do not cause a dispensing movement of the advancement member 8. The pitch $P_1$ of the dosage scale 10a is greater than the pitch of the threads 10b, 9a. In order that the dosage display element 10 moves according to the pitch $P_1$ of the dosage scale 10a on a spiral or helical path that has the same pitch as the dosage scale 10, the threaded sleeve 13 displaces the bearing element 9 by the difference between the pitch $P_1$ and the pitch of the thread 10b. For this purpose, the threaded sleeve 13 can have a thread 13a, 13b that has a pitch that is equal to the difference between the pitch $P_1$ and the pitch of the thread 10b, 9a. In other words, the sum of the pitches of the thread 13a, 13b and the thread 10b, 9a yields the pitch $P_1$ of the dosage scale 10a.

The threaded sleeve 13 is rotatable relative to the advancement member 8 during dose-setting, and is not rotatable relative to the advancement member 8 during dosage dispensing.

In the driving and metering device according to the first embodiment, the threaded sleeve 13 has, in addition to the internal thread 13a, with which the external thread 8a of the advancement member 8 engages, an external thread 13b having the same pitch as the thread 13a. The external thread 13b engages with a thread 4b that is fixed relative to the housing and is formed by the housing 4. This has the effect that threaded sleeve 13 moves relative to the housing 4 along the longitudinal axis L during dose-setting by the same distance as it moves relative to the advancement member 8. Because of the threaded sleeve 13 designed according to the first embodiment, the advancement member 8 need not have a direct threaded engagement with the housing 4.

The clutch member 2 has a longitudinally extending groove 2d, with which an inwardly projecting protrusion 10d of the dosage display element 10 engages, whereby the dosage display element 10 is rotationally fixed relative to the clutch member 2 but is axially movable.

Referring to FIGS. 3a-d, the driving and metering device, which, together with the product container 14 and the product container holder 5, forms an injection device, is shown in an initial position, or in a delivery state, wherein the zero dose is set. The actuating member 7 is not actuated, and the spring 12 presses the actuating member 7 in the proximal direction, so that the second clutch 2b, 16b is engaged and the first clutch 1a, 2a is opened. The spring 11, functioning as a dispensing spring, is preferably preloaded in the delivery state.

By rotating the metering member 3 in the second rotational direction, the clutch member 2 is rotated relative to the housing 4 via the engaged second clutch 2b, 16b, whereby the threaded sleeve 13 screws with its external thread 13b along the housing 4, and with its internal thread 13a along the advancement member 8, more particularly in the proximal direction, whereby it drives the bearing element 9 in the axial direction and the bearing element 9 moves rotationally fixedly in the proximal direction along the housing 4. The dosage display element 10 is conjointly rotated by the rotation of the clutch member 2 and thus screws along the bearing element 9 by means of the thread 10b. The screwing movement of the dosage display element 10 relative to the bearing element 9 is superimposed by the axial movement of the bearing element 9 relative to the housing 4, whereby the dosage display element 10 describes a spiral or helical path relative to the housing 4, which path corresponds to the pitch $P_1$ of the dosage scale 10a. During increasing of the dosage, the maximum-dose stop 10c is moved toward the maximum-dose mating stop 15a. If the maximum dose that can be set with the driving and metering device, indicated here as 60 IU, for example, has been reached, the maximum-dose stop 10c comes into contact with the maximum-dose mating stop 15a (FIGS. 4a-d). The set dose can be corrected or reduced by rotating the metering member 3 in the first direction, wherein the maximum-dose stop 10c is moved away from the maximum-dose mating stop 15a and a zero-dose stop 10e, which is formed by the end face of the dosage display device 10 and functions as an axial stop, is moved toward a zero-dose mating stop 9e, which is formed by a collar of the bearing element 9.

When the metering member 3 is rotated in the first rotational direction, the spring 11 is relaxed. If the user lets go of the metering member 3, the coupling element 16 prevents the spring 11 from relaxing.

To dispense the set dose, the actuating member 7 is displaced in the distal direction against the force of the spring 12, whereby the first clutch 1a, 2a is engaged and the second clutch 2b, 16b is disengaged. The spring 11 now drives the clutch member 2 rotationally in the first rotational direction, wherein the advancement member 8 remains stationary relative to the threaded sleeve 13, the advancement member 8 screwing together with the threaded sleeve 13 in the distal direction by means of the thread 13b on the housing 4 and thus displacing the piston into the product container 14. The engagement member 1c is moved in the process via the toothing 4c, whereby the dispensing movement is signaled by means of clicking sounds. With the toothing 4c, the engagement member 1c additionally forms a unidirectional clutch, which causes the rotation element 1 to be rotatable only in one direction, namely the first rotational direction, which effects dispensing of the product.

Due to the rotation of the clutch member 2 in the first rotational direction, the dosage display element 10 is screwed back on the bearing element 9; in particular, the zero-dose stop 10e is moved in the direction of the zero-dose mating stop 9e, whereby the dosage scale 10a counts back in the indication element 4 to the zero dose. The dispensing is finished when the zero dose is displayed in the indication device 4a (FIGS. 5a-d), or when the zero-dose stop 10e comes into contact with the zero-dose mating stop 9e. FIGS. 5a and 5b show the driving and metering device at the end of dispensing of the product, where the actuating member 7 is still being actuated, i.e., has not yet been released by the user of the device.

By repeated metering and actuation of the actuating'member, the product contained in the product container 14 can be dispensed in several arbitrarily selectable individual dosages.

FIGS. 6a-d show the state of the driving and metering device in which the product container 14 contains a dispensable amount of product that is less than the maximum dose that can be set by the driving and metering device. In the example shown, the product container 14 contains 58 IU, while a maximum of 60 IU can be set with the driving and metering device. To avoid improper usage, the driving and metering device comprises a limiting device, which limits the dose-setting. For this purpose, the advancement member 8 comprises a stop at the proximal end of the thread 8a, against which the threaded sleeve 13 strikes, thus blocking a rotation of the metering member 2 in the first rotational direction, even if the maximum-dose stop 10c is not in contact with the maximum-dose mating stop 15a. A rotation of the metering member 3 in the first rotational direction is possible, however.

In the second embodiment, which is shown in FIGS. 7-12d, the housing 4 has an internal thread 4e, which engages with the external thread 8a of the advancement member 8. In the housing 4, an additional housing insert 18 is arranged, on the inner circumference of which are formed the toothing 4c and the internal thread 4b engaging with the external thread of the threaded sleeve 13. The housing insert 18 additionally forms the zero-dose mating stop 9e, in the form of a rotation stop acting in the circumferential direction.

The rotation element 1 is rotationally fixedly but axially displaceably connected to the advancement member 8. A ridge 1b engages with the groove 8b of the advancement member 8 for this purpose. In contrast to the first embodiment, the threaded sleeve 13 does not have an internal thread, but merely a guide section, on which the threaded sleeve 13 is supported on the thread peaks of the external thread 8a.

FIGS. 9a-9d show the driving and metering device in the initial or delivery state, wherein a dose of zero is set. By rotating the metering member in the second rotational direction, the engaged clutch member 2 is rotated relative to the housing 4 in the second rotational direction via the engaged second clutch 2b, 16b, wherein the dosage indication element 10 is screwed with the aid of the thread 10b in the proximal direction on the bearing element 9. The threaded sleeve 13 is screwed in the proximal direction on the internal thread 4b of the additional housing insert 18, whereby the bearing element 9, guided rotationally fixedly on the housing 4, is displaced in the proximal direction. During dose-setting, the first clutch 2a is disengaged, the clutch member 2 being rotated relative to the advancement member 8.

In FIGS. 10a-d, the maximum dose that can be set with the driving and metering device, 60 IU in the present example, has been set, wherein the maximum-dose stop 10c comes into contact with the maximum-dose mating stop 15a. The dosage can of course be reduced by rotating the metering member 3 in the first rotational direction.

To dispense the set product dose, the actuating member 7 is pressed, whereby the clutch member 2 is displaced in the distal direction relative to the housing 4, wherein the first clutch 1a, 2a is engaged and the second clutch 2b, 16b disengaged.

In particular, the clutch member 2 has a collar in the region on which the clutch structure 2a is formed, the collar holding the engagement member 1c in engagement with the toothing 4c in the unactuated state, whereby the rotation element 1, and thus the piston rod 8, is prevented from rotating relative to the housing 4. By actuating the actuating member 7, the engagement member 1c is also released, i.e., the collar is moved out of engagement with the engagement member 1c. By disengaging the second clutch 2b, 16b, the clutch member 2 is rotated by the drive spring 11 in the first direction, whereby the rotation element 1, which engages rotationally fixedly but axially movably with the advancement member 8, is rotated relative to the housing 4 and also rotates the advancement member 8. The advancement member 8 screws via its external thread along the internal thread 4e of the housing 4 in the distal direction, whereby the piston is displaced into the product container 14.

During dispensing of the product, the dosage display element 10 rotates back into its zero-dose position, i.e., the zero-dose stop 10e is moved towards the zero-dose mating stop 9e, the dosage scale 10a counting down in the direction of zero in the indication device 4*a*. Dispensing is finished when the zero dose appears in the indication device 4*a* or/and the zero-dose stop 10*e* comes into contact with the zero-dose mating stop 9*e*. FIGS. 11*a-d* show the driving and metering device after dispensing of the product has been accomplished, wherein the actuating member 7 is still being actuated.

By repeated metering and actuation of the actuating member 7, the product contained in the product container 14 can be dispensed in several freely selectable individual doses.

FIGS. 12*a-d* show the driving and metering device in the state that corresponds to the state of FIGS. 6*a-d*. To prevent rotation of the metering member 3 in the second rotational direction, an intermediate sleeve 19 is arranged between the threaded sleeve 13 and a limit stop of the advancement member 8. The intermediate sleeve 19 can engage with the groove 8*b*, for example, wherein the proximal end of the groove 8*b* can form the limit stop. Alternatively, the intermediate sleeve 19 can engage via an internal thread with the external thread 8*a*, wherein the limit stop can be formed at the end of a thread flight.

The third embodiment, from FIGS. 13-18*d*, has a threaded sleeve 13, which engages via its internal thread 13*a* with the external thread 8*a* of the advancement member 8, and in particular, has no external thread. The housing 4 further comprises an internal thread 4*e* that engages with the external thread 8*a* of the advancement member 8, so that a rotational movement of the advancement member 8, more particularly in the first direction, effects a movement of the advancement member 8 in the dispensing direction, i.e., in the distal direction. The housing insert 15 further comprises an external thread 15*c*, with which a limiter 17 in the form of a circular segment engages. On its concave surface, the limiter 17 additionally has a thread, with which the thread 15*c* is engaged. The limiter 17 is rotationally fixed to the metering member 3, so that the limiter 17 is rotated along with the metering member 3 about the housing insert 15.

The limiter 17 is used for preventing the setting of a dose that exceeds the dispensable product dose contained in the product container 14.

FIGS. 15*a*-15*d* show the driving and metering device in the initial or delivery state. To set the product dose, the metering member 3 is rotated relative to the housing 4, whereby the clutch member 2 is rotated relative to the housing 4 via the engaged second clutch 2*b*, 16*b*. The clutch member 2 rotates the threaded sleeve 13, which thereby screws along the longitudinal axis L on the advancement member 8. By means of a protrusion and a longitudinal guide groove (not shown), the threaded sleeve 13 is also rotationally fixedly but axially movably engaged with the dosage display element 10, whereby the dosage display element 10 is rotated along with the clutch member 2 and the threaded sleeve 13. The threaded sleeve 13 additionally drives the bearing element 9, which is rotationally fixed and axially displaceable on the housing 4, along the longitudinal axis L.

In the region of the clutch structure 2*a*, the clutch member 2 comprises the collar described in connection with the second embodiment, said collar keeping the engagement member 1*c* engaged with the toothing 4*c* when the actuating member 7 has not been actuated, and releasing it when the actuating member 7 has been actuated. Thus the rotation element 1 and the piston rod 8 are secured against rotation relative to the housing 4 during the dose-setting.

During dose-setting, particularly when the metering member 3 is being rotated in the second rotational direction, i.e., for increasing the dosage, the limiter 17 is moved toward a limit stop that is formed by the metering member 3. The distance from the limit stop is proportional to the amount of dispensable product contained in the product container 14. If the metering member 3 is rotated in the first rotational direction, the limiter 17 is moved away from the limit stop.

FIGS. 16*a-d* show the driving and metering device with a maximum settable dosage, 80 IU in the present example, wherein the maximum-dose stop 10*c* comes into contact with the maximum-dose mating stop 15*a*. The set dose can, of course, be reduced by rotating the metering member 3 in the first rotational direction.

To dispense the set dose, the actuating member 7 is pressed, whereby the first clutch 1*a*, 2*a* is engaged and the second clutch 2*b*, 16*b* is disengaged, and the spring 11 rotates the clutch member 2 in the first rotational direction. Due to the engaged first clutch 1*a*, 2*a*, the clutch member 2 rotates the rotation element 1, which in turn rotates the advancement member 8, whereby the advancement member 8 is screwed in the axial direction via its external thread 8*a* on the thread 4*e* of the housing 4 and the piston is displaced in the product container 14. During dose dispensing, the dosage display element 10 screws back in the direction of the zero position. The dispensing is finished when the zero-dose stop 10*e* of the dosage display element 10 comes into contact with the zero-dose mating stop 9*e*, which is formed by the housing 4, or/and the zero dose appears in the indication device 4*a*.

During dispensing of the product, the metering member 3 does not rotate relative to the housing 4, because the actuating button 7 is coupled to the toothing 15 by means of protrusions/engagement members 7*a*. Thereby the limiter 17 retains its position in relation to the limit stop, whereby in particular a counter is formed, which counts while setting the dose but does not count while dispensing the dose.

By repeated metering and actuation of the actuating member 7, the product contained in the product container 14 can be dispensed in several freely selectable individual doses.

FIGS. 18*a-d* show the driving and metering device in a state in which the maximum settable dose exceeds the quantity of product contained in the product container 14. To prevent dispensing of a quantity of product greater than that which can be dispensed from the container 14, the limiter has moved during the individual dispensing processes sufficiently close to the limit stop that it comes into contact with the limit stop, whereby a rotation of the metering member 3 relative to the housing 4 in a second direction is prevented. A rotation of the metering member 3 in the first rotational direction is still possible, however.

The invention claimed is:

1. A driving and metering device for an injection device for dispensing a liquid product, wherein a product dose to be dispensed can be set with the driving and metering device, comprising:
    a dosage display element comprising a helical dosage scale arranged over a circumference;
    an indication device;
    a metering member that can be gripped by the user of the driving and metering device; and
    a bearing element comprising a thread in a threaded engagement with a thread of the dosage display element,
    wherein the dosage display element can be screwed relative to the indication device about an axis of rotation (L) by rotating the metering member relative to the indication device in order to set the dose to be dispensed and is movable relative to the metering member along the axis of rotation (L), wherein a value of the dosage scale that corresponds to the set dose can be read by means of the indication device, wherein a thread pitch of the thread of the dosage display element is not equal to a pitch of the helical dosage scale, and wherein the driving and metering device further comprises a threaded sleeve rotatably and axially fixedly coupled to the bearing element.

2. The driving and metering device of claim 1, wherein the threaded sleeve is connected rotationally fixedly and axially movably to a clutch member, and wherein the dosage display element is rotationally fixed relative to the clutch member but is axially movable.

3. The driving and metering device of claim 1, further comprising a housing, wherein the bearing element is rotationally fixed and axially displaceable relative to the housing.

4. The driving and metering device of claim 3, wherein the threaded sleeve comprises an internal thread in a threaded engagement with a thread of an advancement member.

5. The driving and metering device of claim 4, wherein a sum of the thread pitch of the thread of the dosage display element and of a thread pitch of the internal thread of the threaded sleeve is equal to the pitch of the helical dosage scale of the dosage display element.

6. The driving and metering device of claim 4, wherein the threaded sleeve comprises an external thread in a threaded engagement with a thread fixed relative to the housing.

7. The driving and metering device of claim 6, wherein a sum of the thread pitch of the thread of the dosage display element and of the thread pitch of the external thread of the threaded sleeve is equal to the pitch of the helical dosage scale of the dosage display element.

8. The driving and metering device of claim 4, wherein the threaded sleeve is rotatable relative to the advancement member during dose-setting and is rotationally fixed relative to the advancement member during dispensing of the product.

9. The driving and metering device of claim 4, further comprising a drive spring configured to drive the advancement member during dispensing of the product, wherein the drive spring is at least one of preloaded or can be cocked by rotating the metering member.

10. The driving and metering device of claim 9, further comprising a releasable blocking device arranged between the metering member and the clutch member such that torque exerted by the drive spring onto the clutch member is directed into the housing, so that the clutch member is inhibited against rotation relative to the housing, wherein such rotational inhibition of the clutch member can be released by rotation of the metering member, so that the clutch member becomes rotatable relative to the housing in at least a first rotational direction.

11. The driving and metering device of claim 1, wherein the dosage display element is rotationally fixedly and axially displaceably connected to a clutch member, said clutch member rotatable relative to the indication device during dose-setting and during dispensing of the product.

12. The driving and metering device of claim 11, further comprising an actuating member that can be actuated to dispense product and a first clutch, wherein the first clutch is disengaged when the actuating member is not actuated and is engaged when the actuating member has been actuated, or is engaged by actuating the actuating member, wherein, when engaged, the first clutch couples the clutch member and the advancement member rotationally fixedly to one another, and wherein, when the first clutch is disengaged, the clutch member is uncoupled from the advancement member such that the clutch member is rotatable relative to the advancement member.

13. The driving and metering device of claim 12, further comprising a clutch spring that tensions or presses the first clutch such that it is disengaged when the actuating member has not been actuated.

14. The driving and metering device of claim 12, further comprising a second clutch, which is engaged when the actuating member has not been actuated and is disengaged when the actuating member has been actuated, or is disengaged by actuating the actuating member, wherein, when engaged, the second clutch couples the metering member and the clutch member rotationally fixedly in at least one rotational direction, and wherein, when the second clutch is disengaged, the metering member is uncoupled from the clutch member such that the clutch member is rotatable relative to the metering member.

15. The driving and metering device of claim 14, further comprising a clutch spring that tensions or presses the first clutch such that it is disengaged and/or tensions or presses the second clutch such that it is engaged when the actuating member has not been actuated.

16. The driving and metering device of claim 11, further comprising an actuating member that can be actuated to dispense product and a second clutch, which is engaged when the actuating member has not been actuated and is disengaged when the actuating member has been actuated, or is disengaged by actuating the actuating member, wherein, when engaged, the second clutch couples the metering member and the clutch member rotationally fixedly in at least one rotational direction, and wherein, when the second clutch is disengaged, the metering member is uncoupled from the clutch member such that the clutch member is rotatable relative to the metering member.

17. The driving and metering device of claim 16, further comprising a clutch spring that tensions or presses the second clutch such that it is engaged when the actuating member has not been actuated.

18. The driving and metering device of claim 1, further comprising a mechanism for preventing the setting of a dose that exceeds the amount of a product in the product container.

* * * * *